US012257381B2

United States Patent
Jung et al.

(10) Patent No.: US 12,257,381 B2
(45) Date of Patent: Mar. 25, 2025

(54) SYSTEM, CARTRIDGE AND PROCESS

(71) Applicant: Boehringer Ingelheim International GmbH, Ingelheim am Rhein (DE)

(72) Inventors: Andree Jung, Idar-Oberstein (DE); Stephen Terence Dunne, Oporto (PT); Joachim Carl Herbert Eicher, Ingelheim am Rhein (DE)

(73) Assignee: BOEHRINGER INGELHEIM INTERNATIONAL GMBH, Ingelheim am Rhein (DE)

( * ) Notice: Subject to any disclaimer, the term of this patent is extended or adjusted under 35 U.S.C. 154(b) by 952 days.

(21) Appl. No.: 16/973,064

(22) PCT Filed: Jun. 12, 2019

(86) PCT No.: PCT/EP2019/065344
§ 371 (c)(1),
(2) Date: Dec. 8, 2020

(87) PCT Pub. No.: WO2019/238749
PCT Pub. Date: Dec. 19, 2019

(65) Prior Publication Data
US 2021/0268213 A1    Sep. 2, 2021

(30) Foreign Application Priority Data
Jun. 15, 2018  (EP) ..................... 18177967

(51) Int. Cl.
*A61M 15/00* (2006.01)
*A61M 5/24* (2006.01)
*A61M 11/00* (2006.01)

(52) U.S. Cl.
CPC ...... *A61M 15/0003* (2014.02); *A61M 5/2448* (2013.01); *A61M 11/007* (2014.02); *A61M 15/0065* (2013.01); *A61M 2202/08* (2013.01)

(58) Field of Classification Search
CPC ........... A61M 2005/2451; A61M 15/00–0003; A61M 11/00; A61M 11/006–007;
(Continued)

(56) References Cited

U.S. PATENT DOCUMENTS

| 5,836,479 A | 11/1998 | Klima |
| 6,481,435 B2 | 11/2002 | Hochrainer |

(Continued)

FOREIGN PATENT DOCUMENTS

| AU | 2003234744 A1 | 9/2003 |
| CN | 101426543 A | 5/2009 |

(Continued)

OTHER PUBLICATIONS

International Search Report for corresponding PCT Application No. PCT/EP2019/065344, 8 pages, Oct. 2, 2019.

*Primary Examiner* — Rachel T Sippel
(74) *Attorney, Agent, or Firm* — Calderon Safran & Wright P.C.; David S. Safran

(57) ABSTRACT

A cartridge for a dispensing device, such as a nebulizer, for dispensing a medicament composed of or produced from a plurality of components and a system including a dispensing device, such as a nebulizer, and such a cartridge. The cartridge includes at least two fluidically separated chambers which each contain at least one component of the medicament, an actuating mechanism for fluidically connecting the chambers and mixing the components for the dispensing of the medicament. A method for preparing a medicament composed of a plurality of components in a cartridge for the dispensing of said medicament by way of a dispensing device, such as a nebulizer, where a plurality of fluidically separated chambers of the cartridge are fluidically connected, and a component of the medicament is at least partially transferred from one of the chambers to another of the chambers with another component of the medicament in (Continued)

Figure 1:
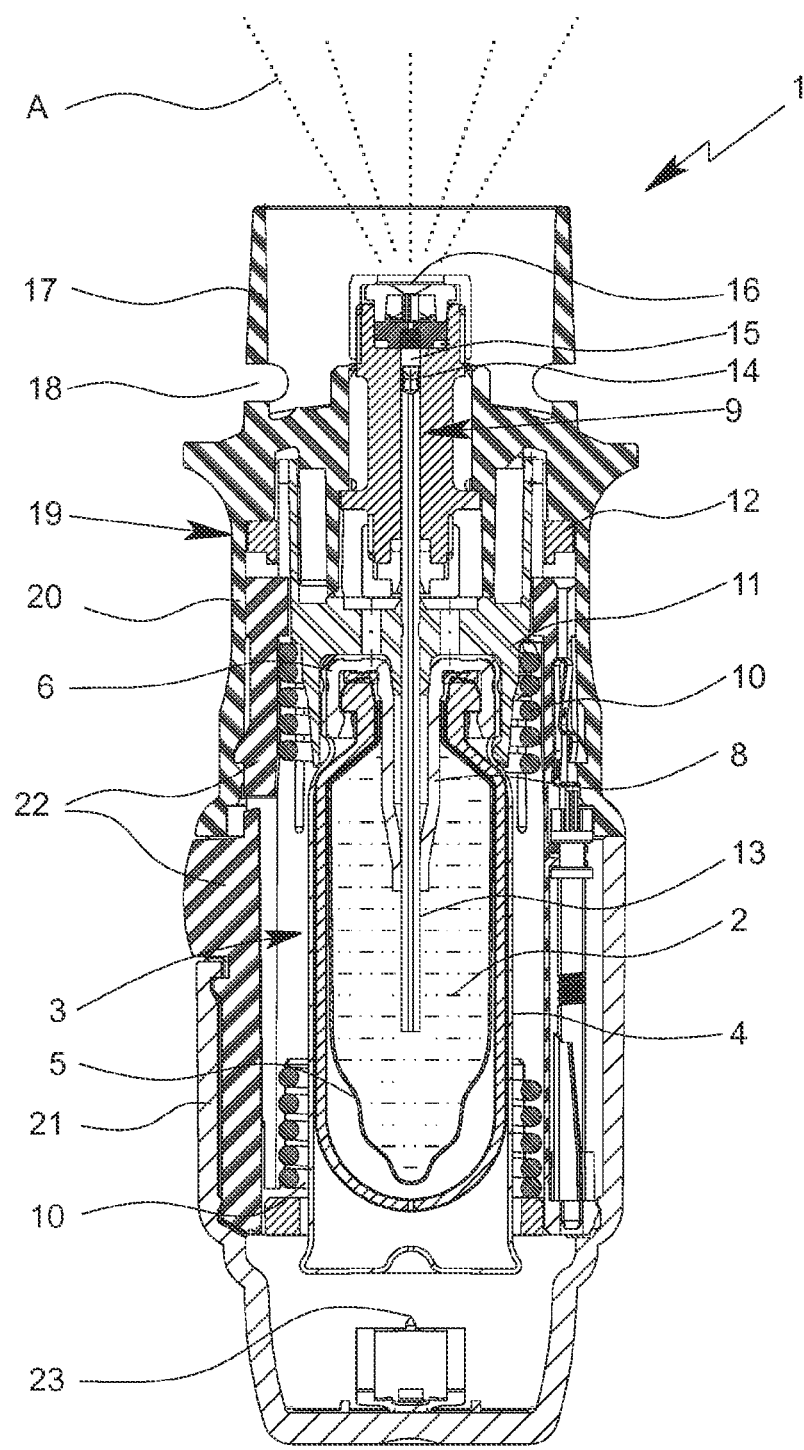

order to mix the components. Only once the components have been mixed is the cartridge opened for the extraction of a dose of the medicament.

35 Claims, 16 Drawing Sheets

(58) Field of Classification Search
CPC ...... A61M 11/02; A61M 11/06; A61M 11/08; A61M 5/2053; A61M 5/2066; A61M 5/24; A61M 5/2448–2466; A61M 5/28–281; A61M 5/284–288; A61M 2005/2407; A61M 2005/2414; A61M 2005/2422; A61M 2005/3117–3121; A61M 2005/247–2474; A61M 2005/2485–2488
See application file for complete search history.

(56) References Cited

U.S. PATENT DOCUMENTS

| | | | |
|---|---|---|---|
| 6,626,379 | B1 | 9/2003 | Ritsche |
| 7,021,561 | B2 | 4/2006 | Vedoriinu |
| 7,213,593 | B2 | 5/2007 | Hochrainer |
| 2001/0009151 | A1 | 7/2001 | Hochrainer |
| 2001/0032643 | A1 | 10/2001 | Hochrainer |
| 2003/0111552 | A1 | 6/2003 | Vedoriinu |
| 2006/0178641 | A1 | 8/2006 | Reynolds |
| 2009/0105685 | A1 | 4/2009 | Stroem Hansen |
| 2009/0131864 | A1 | 5/2009 | Pickhard |
| 2011/0166549 | A1 | 7/2011 | Hunter |
| 2013/0197467 | A1 | 8/2013 | Schuetz |
| 2017/0203056 | A1 | 7/2017 | Dunne |
| 2018/0085517 | A1 | 3/2018 | Laurence |
| 2020/0197630 | A1 | 6/2020 | Petit |

FOREIGN PATENT DOCUMENTS

| | | |
|---|---|---|
| CN | 208552759 U | 3/2019 |
| CN | 110719794 A | 1/2020 |
| DE | 202004005433 U1 | 7/2004 |
| EP | 0599649 A1 | 6/1994 |
| EP | 0568321 A2 | 7/1998 |
| EP | 1616591 A2 | 1/2006 |
| EP | 1707495 A1 | 10/2006 |
| EP | 2801530 A2 | 11/2014 |
| EP | 3205228 A1 | 10/2020 |
| GB | 0158441 A2 * | 3/1984 |
| JP | 2010017567 A | 1/2010 |
| JP | 2014028082 A | 2/2014 |
| WO | 9739831 A1 | 10/1997 |
| WO | 0023037 A1 | 4/2000 |
| WO | 2006006963 A2 | 1/2006 |
| WO | 2012162305 A1 | 11/2012 |
| WO | 2015169431 A2 | 11/2015 |
| WO | 2016043601 A1 | 3/2016 |

* cited by examiner

SYSTEM, CARTRIDGE AND PROCESS

BACKGROUND

The present patent application relates to a cartridge for a dispensing device or a nebulizer, to a system, and to a method for preparing a fluid for dispensing or nebulization.

The present invention relates to the nebulizing or dispensing of a fluid, preferably a liquid, in particular a liquid medicament or a liquid medicament composition, to a user or patient by means of a dispensing device, preferably a mechanical nebulizer, and a preferably replaceable cartridge that contains the fluid to be nebulized.

In order to extend the shelf life of a medicament intended to be dispensed or nebulized, in particular to at least two or three years, and/or to counteract adverse changes in a medicament that occur in particular when the medicament is stored for a relatively long time, individual components of the medicament can be stored separately in a cartridge and brought into contact or mixed with one another shortly or immediately before using the nebulizer or before the nebulization.

The separately stored components of the medicament can have different physical states and/or be present in the cartridge in a liquid, gaseous or solid, in particular powdery, form. For example, a first component of the medicament can be a solid medicinal agent, preferably in powder form, and a second component of the medicament can be a solvent, in particular a liquid solvent.

In particular, the medicinal agent can be present in different physicochemical states or in a solid, liquid, dissolved or suspended state.

WO 97/39831 A1 discloses a cartridge having two chambers for the separate storage of the active ingredient and the solvent of a medicament. When the cartridge is inserted into a nebulizer for nebulizing the medicament, the chamber with the active ingredient is pierced by means of a cannula so that the active ingredient comes into contact with the solvent and is dissolved. The storage time of the medicament is extended by the separate storage of the active ingredient and the solvent.

WO 00/23037 A1 likewise discloses such a cartridge for a nebulizer with the cartridge comprising two chambers for the separate storage of individual components of a medicament.

US 2003/0111552 A1 shows a spray device having a spray nozzle, a sleeve and at least two spaced-apart stoppers which are arranged in the sleeve and define a first and a second chamber of the sleeve, each of which contains a substance. A plunger connected to the first stopper can be pushed into the sleeve. This moves the plungers in the sleeve so that a bypass is released, and the substances in the two chambers mix together. By pushing the plunger further, the mixed substance is dispensed through the spray nozzle. The device can have a cap for closing the spray nozzle with said cap either being removed before the actuation of the spray device or having air channels so that air can escape during the mixing process.

EP 0 568 321 A2 relates to a pre-filled syringe. The syringe comprises a tubular body having an injection needle on one side and a plunger on the other side as well as a separating piece arranged in between. The separating piece divides the interior of the tubular body into two separate chambers, each of which contains a substance. Furthermore, the tubular body has a bypass in order to mix the substances in the chambers before the injection in that the separating piece is displaced by pressure on the plunger in such a way that it is arranged adjacent to the bypass.

US 2013/0197467 A1 relates to a sealed container, in particular a multi-chamber syringe. The syringe comprises a sleeve having a bypass and three plungers which divide the interior of the sleeve into three chambers, with two of the chambers containing substances to be mixed. By pushing down a plunger rod, the plungers are displaced such that the substances can be mixed via the bypass. U.S. Pat. No. 6,626,379 B1 relates to a dispensing device for pharmaceutical products. The dispensing device comprises a first chamber with a solid near the dispensing opening and a second chamber with a liquid substance on an underside facing away from the dispensing opening. The second chamber is sealed by a stopper. By exerting pressure on the underside, a needle is inserted through the stopper, and the second chamber is opened to the environment. By further exertion of pressure, the liquid is guided from the second chamber into the needle and further into the first chamber where it mixes with the solid substance and is then dispensed. In an alternative embodiment, the first chamber is arranged between the stopper and the second chamber with an additional plunger separating the two chambers from one another. When actuated, the stopper is first pierced, thus opening the first chamber to the environment. The plunger is then pushed down so that a bypass opens, and the substances are mixed with one another before they are guided through the needle to the dispensing opening.

EP 3 205 228 A1 relates to a cosmetic container for mixing two cosmetic liquids. The container has a rigid main body in which the first liquid is located and a collapsible pocket at the lower end of the main body in which the second liquid is located. There is a one-way valve between the main body and the pocket. By squeezing the pocket, the second liquid is forced through the valve into the main body where it mixes with the first liquid.

EP 1 707 495 A1 relates to a device for holding and mixing two cosmetics, in particular for producing a cosmetic hair treatment product. The device comprises a container having an opening and a first liquid. An intermediate part is attached to the container opening onto which a closure unit is screwed so that the container is closed. A chamber with a second liquid is formed between the intermediate part and the closure unit. By partially unscrewing the closure unit, the chamber is opened toward the container opening so that the second liquid flows into the container and mixes with the first liquid. The closure unit can then be unscrewed completely and a dispensing part can be inserted into the container for the metered delivery of the mixed liquid.

U.S. Pat. No. 5,836,479 A relates to a refillable dispensing device, in particular a spray bottle. The device has a container and one or more reservoirs for chemicals. The container can be filled with water, and then the reservoir or one of the reservoirs can be opened toward the container in order to produce a dilute chemical solution. According to one embodiment, the reservoir is designed as a cap. Two chambers, each containing a chemical, are formed in the cap. By rotating the cap, the walls of the chambers break so that the chemicals mix and are delivered into the container.

SUMMARY

The present invention is based on the object of providing an improved system, an improved cartridge and an improved method for preparing a fluid composed of a plurality of components to be dispensed or nebulized, preferably wherein a simple, fast, safe, hygienic, reliable and/or homogeneous mixing of components of a medicament which are stored fluidically separated from one another is made possible or supported.

The above object is achieved by a cartridge, by a system and/or by a method as disclosed.

By means of the proposed system, it is preferably possible to nebulize a fluid or a medicament or deliver it to a user or a patient, in particular in the form of an aerosol.

The proposed system preferably comprises a dispensing device and a cartridge, in particular wherein the cartridge contains a plurality of components of a fluid or a medicament and/or is or can be fluidically connected to the dispensing device.

The system is preferably designed as a kit with the kit containing the dispensing device and at least one cartridge.

A kit within the meaning of the present invention is, in particular, a unit and/or a system comprising the dispensing device and at least one cartridge. The dispensing device and the cartridge preferably each form one component of the kit. The components of the kit are preferably placed on the market together, in particular in a shared package or the like. However, it is also possible for the components mentioned to form a loose combination for joint use. A shared or connecting component is preferably provided, for example, instructions for use, recommendations for action or references in the labels of one or more of the components of the kit or the shared packaging.

A dispensing device within the meaning of the present invention is preferably a device for administering or dispensing a fluid or medicament to a user or patient, preferably wherein the medicament is applied aurally, inhalatively, intraocularly, intranasally, intramuscularly, intravenously, orally, percutaneously, subcutaneously, sublingually and/or subconjunctivally. A dispensing device within the meaning of the present invention is preferably realized as a nebulizer, an inhaler, a syringe or the like. The following statements relate in particular to nebulizers but also apply accordingly to other dispensing devices.

The dispensing device, in particular the nebulizer, preferably has a housing for accommodating the cartridge and a pump, which is preferably designed to remove a dose of the fluid from the cartridge and to apply pressure to the corresponding dose for the nebulization of the fluid.

The proposed cartridge preferably has a container and a closure for the fluidic and/or sealing connection of the container to the nebulizer with the cartridge, preferably wherein the cartridge, in particular the container, has at least two fluidically separated, in particular closed, chambers, each of which contains at least one component of the fluid or medicament.

One aspect of the present invention is that the cartridge has an actuating mechanism that is preferably at least partially removable from the cartridge, in particular from the container or closure, with the chambers being able to be opened or fluidically connected to one another by actuating the actuating mechanism, in particular to bring the components stored separately in the cartridge into contact with one another or to mix them so that the fluid can be dispensed or nebulized, and/or to produce the fluid in the cartridge or in one of the chambers, in particular by mixing the components.

A component of a fluid or medicament within the meaning of the present invention is preferably a substance, in particular a pure substance or a mixture of substances, which is, in particular together with a further component, required for the production and/or generation of the fluid or medicament. In particular, a medicament can be produced or prepared or generated by bringing together or bringing into contact and/or mixing or blending a plurality of components.

A component within the meaning of the present invention is, in particular, a starting material for the production of the medicament, preferably wherein the starting material does not enter into a chemical reaction during the production of the medicament or is not consumed and/or is present as a component of the produced medicament after the production of the medicament. However, it is also possible that the component or starting material enters into a chemical reaction during the production of the medicament or is at least partially or completely consumed.

The finished and/or ready-to-be-dispensed and/or produced and/or generated medicament is particularly preferably a mixture of at least two components and/or a product produced by at least one chemical reaction of at least two components.

In particular, a component of a medicament within the meaning of the present invention can be a starting material and an auxiliary or additive substance, in particular a pharmaceutical auxiliary or additive substance, such as a solution, in particular an ethanolic solution, a solvent, a solubilizer, a buffer, in particular an aqueous buffer, a preservative, a suspending agent or the like and/or a medicinally active or pharmacologically active ingredient (active ingredient or medicinal agent) and/or contain such an agent or substance.

The active ingredient or an active ingredient or medicinal agent may come, for example, from the group of peptide hormones, peptide medicinal agents such as insulin, erythropoietin or the like, the group of anticholinergics such as ipratropium bromide, oxitropium bromide, aclidinium bromide, glycopyrronium bromide, tiotropium bromide or the like, which are particularly short and/or long-acting, the group of beta-2-sympathomimetic agents such as salbutamol, fenoterol, terbutaline, arformoterol, indacaterol, formoterol, olodaterol, salmeterol, vilanterol, tulobuterol or the like, which are particularly fast, short and/or long-acting, the group of glucocorticoids such as budesonide, ciclesonide, fluticasone, beclometasone or the like, the group of aminoglycosides such as tobramycin or the like and/or the group of steroids.

Combinations of a plurality of active ingredients or groups are preferably possible as well. The medicament or a component of the medicament can, in particular, contain a plurality of active ingredients or groups of active ingredients, for example from the group of glucocorticoids, beta-2-sympathomimetics and/or anticholinergics.

Lactose, mannitol, lecithin, cholesterol, polyethylene glycol, glycerol or ethanol, for example, can be used as an auxiliary or additive substance.

The components that are stored separately from one another preferably differ with regard to at least one, in particular, physicochemical property of the substance such as chemical structure, density, physical state, viscosity (especially if two different solvents are required), pH, molecular weight or the like. In particular, one component can be present in a dissolved state, and another component can be present in an undissolved state.

One component of the at least two components of the medicament is particularly preferably solid, preferably dried, in particular freeze-dried or lyophilized, and/or in powder form and/or (partially) encapsulated.

One component of the at least two components of the medicament is particularly preferably present in the form of liposomes, in particular freeze-dried or lyophilized liposomes, or as a liposomal formulation, in particular a freeze-dried or lyophilized liposomal formulation, preferably in order to extend the duration of action.

One component, in particular a medicament or the medicament, is preferably enclosed in liposomes, in particular freeze-dried or lyophilized liposomes, or embedded in the interior of the liposomes and/or in the membrane of the liposomes.

For example, lipophilic or hydrophobic active ingredients and/or active ingredients with low or poor solubility in water and/or high or good solubility in ethanol, such as active ingredients from the group of glucocorticoids, can be or will be enclosed in liposomes, in particular in the membrane of liposomes.

Additionally or alternatively, lipophobic or hydrophilic active ingredients and/or active ingredients with high or good solubility in water and/or low or poor solubility in ethanol, such as active ingredients from the group of beta-2 sympathomimetics, can be or will be enclosed in the interior or in the core of the liposomes.

One (other) component of the at least two components of the medicament is preferably liquid or in the form of a liquid. However, it is also possible that both or all the components are liquid or are contained in the cartridge as a liquid.

The components preferably have different (dynamic) viscosities and/or one component is highly viscous or has a component with a (dynamic) viscosity of more than 1 or 1.5 mPas, particularly preferably more than 2 or 2.5 mPas, and/or less than 50 or 40 mPas, particularly preferably less than or 20 mPas. The (dynamic viscosity) of the medicament produced by mixing the components is preferably more than 1 or 1.5 mPas and/or less than 30 or 20 mPas, in particular less than 15 or 10 mPas.

The (dynamic) viscosity is preferably determined at a temperature of 20° C. and/or a pressure of 101.325 kPa and/or in accordance with DIN 53019-1:2008-09, DIN 53019-2:2001-02 and/or DIN 53019-3:2008-09.

According to a further aspect of the present invention that can also be realized independently, the cartridge is designed to produce a liposomal formulation as a medicament or a liposomal medicament or liposomes, in particular in one of the chambers of the cartridge, in particular by actuating the actuating mechanism.

A first chamber of the cartridge preferably contains an in particular ethanolic lipid solution as the first component of the medicament, and a second chamber of the cartridge contains an aqueous buffer as the second component, in particular to produce a liposomal formulation as a medicament or a liposomal medicament or liposomes by actuating the actuating mechanism and/or by bringing the components in contact with one another.

It can be provided in particular that at least one active ingredient or medicinal agent (in each case) is contained in the lipid solution and/or in the aqueous phase. A lipophilic or hydrophobic active ingredient, such as from the group of glucocorticoids, and/or a lipophobic or hydrophilic active ingredient in the aqueous phase, such as from the group of beta-2 sympathomimetics, can be contained in the lipid solution, for example.

With the proposed cartridge, it is possible to mix the components exclusively by means of the cartridge or independently of the dispensing device or the nebulizer or other devices and/or outside the dispensing device or the nebulizer, in particular to produce the medicament. This makes possible or supports a particularly simple, hygienic, safe, homogeneous and/or rapid mixing of the components.

In particular, it is possible to mix the components immediately before using the cartridge and/or to produce a liposomal formulation as a medicament or medicinal agents embedded in liposomes immediately before using the cartridge or the nebulizer with the cartridge.

The chambers are particularly preferably fluidically connectable to one another and/or openable with respect to one another in the closed state of the cartridge or the container, i.e., in the state where they are sealed against the outside or the environment, in particular in a gastight and/or liquid-tight state, in particular by actuating the actuating mechanism. In this way, a sterile or hygienic mixing of the components is made possible or supported. In particular, liquid is prevented from leaking during the mixing process.

An actuating mechanism within the meaning of the present invention is preferably a structural device for mixing the components of the fluid that are separately present in the cartridge. In particular, the mixing process can be activated or initiated and/or—preferably completely-carried out by actuating the actuating mechanism, most particularly preferably independently of the dispensing device or the nebulizer and/or outside the dispensing device or the nebulizer and/or before inserting the cartridge into the dispensing device or the nebulizer.

The actuating mechanism can preferably be actuated manually or by a user, particularly preferably by turning, pressing, removing and/or opening the actuating mechanism or an actuating element of the actuating mechanism, in particular immediately before the nebulizer is used for the first time.

The actuating mechanism is preferably connected to the cartridge and/or fastened to the cartridge, in particular in a form-fit, force-fit and/or cohesive manner. It is particularly preferred that the actuating mechanism is detachable from the cartridge or the container or the closure and/or is detachably connected to the cartridge or detachably attached to the cartridge.

In particular, the actuating mechanism for inserting the cartridge into the nebulizer is removable and/or the actuating mechanism is removed from the cartridge, in particular the container or the closure, after the components of the fluid have been mixed and before the cartridge is inserted into the nebulizer. Alternatively, the cartridge is inserted into the nebulizer together with the actuating mechanism, in particular after the components have been mixed. In particular, the actuating mechanism can be integrated into the cartridge, particularly preferably into the bottom of the container and/or into the closure of the cartridge.

The actuating mechanism is, in particular after actuation of the actuating mechanism or after the opening or fluidic connection of the chambers, preferably removable from the container and/or the closure of the cartridge, in particular in a rotatable or detachable manner, preferably to open the cartridge toward the outside or vis-a-vis the environment and/or to insert the cartridge into the nebulizer. This makes possible a particularly compact design of the nebulizer or an increase in the fluid volume since the actuating mechanism does not have to be accommodated by the nebulizer.

The cartridge, in particular the container, preferably has at least one or two movable or displaceable plungers, preferably wherein the plunger(s) is/are displaceable in the cartridge or in the container by actuating the actuating mechanism and/or (each) forming a wall of the chamber for the components of the medicament.

One of the chambers or all of the chambers can, in particular, be reduced in size by actuating the actuating mechanism, preferably by moving the plungers, in particular, in order to fluidically connect the chambers to one another and/or to mix the components.

In a particularly preferred embodiment, the chambers can be fluidically connected to one another by actuating the actuating mechanism preferably automatically, i.e., without any further action on the part of a user or a patient. In particular, one of the components can be automatically transferred from one chamber to the other by actuating the actuating mechanism. Particularly preferably, a mixing process in the cartridge is initiated or triggered and/or automatically continued or completed by actuating the actuating mechanism. In this way, a particularly simple and/or user-friendly mixing of the components is made possible or supported.

The actuating mechanism is preferably designed to hold the plunger(s) in position in the cartridge in the non-actuated state of the actuating mechanism or to secure it/them against displacement. In particular, the plunger(s) in the cartridge can be released by actuating the actuating mechanism, in particular in such a way that the plunger(s) is/are displaced in the cartridge automatically, preferably by a force acting in the direction of one of the chambers, particularly preferably by a tensile force, in particular generated in the chambers by negative pressure.

Alternatively, the actuating mechanism is preferably mechanically coupled to the plunger(s), in particular via a connecting part such as a threaded rod, in order to move the plunger(s) or reduce in size at least one of the chambers.

According to a further aspect of the present invention, which can also be realized independently, the dispensing device or the nebulizer is designed to fluidically connect the chambers and/or mix the components to provide and/or nebulize the fluid in the unopened state of the cartridge or the container or in the state where they are sealed against the outside or against the environment, in particular in the gastight and/or liquid-tight state, for example by first actuation of the dispensing device or the nebulizer and/or the actuating mechanism. Corresponding advantages are achieved in this way.

By means of the proposed dispensing device or the proposed nebulizer, it is preferably possible to fluidically connect the chambers to one another after and/or by the insertion of the cartridge into the dispensing device or the nebulizer and to then, or only after the components have been mixed, to open the cartridge toward the outside or vis-a-vis the environment to extract a dose of the fluid produced in the cartridge.

In the proposed method for preparing or providing a medicament to be dispensed or nebulized, a plurality of chambers of the cartridge that are initially fluidically separated from one another are opened with respect to one another or fluidically connected to one another, and the components of the medicament contained therein are preferably completely mixed, in particular in order to produce the medicament in the cartridge or one of the chambers by bringing together or mixing the components, preferably wherein the cartridge is not opened to the outside or vis-a-vis the environment until the chambers are fluidically connected, and/or in particular after the components have been mixed completely for the extraction of a dose of the medicament and/or inserted in the dispensing device or the nebulizer and/or fluidically connected to the dispensing device or the nebulizer. Corresponding advantages are realized in this way.

The cartridge is particularly preferably closed or sealed completely, in particular in a gastight and/or liquid-tight manner, after mixing or before opening. A fluidic connection, in particular of the chamber(s), to the outside or to the environment or to the dispensing device is only created when the cartridge is opened.

The proposed method makes possible or supports a particularly hygienic or sterile, reliable and/or homogeneous mixing of the components and thus an improved preparation of the medicament for delivery or nebulization by means of the dispensing device or nebulizer.

The components of the medicament are particularly preferably mixed outside the dispensing device or the nebulizer and/or independently of the dispensing device or the nebulizer, in particular by actuating the actuating mechanism.

According to a first variant of the proposed method, the cartridge is, after the components have been mixed, first opened outside the nebulizer toward the outside or to extract a dose of the fluid, for example by removing the actuating mechanism, and/or, after the components have been mixed, the actuating mechanism is initially removed from the cartridge, in particular the container and/or the closure of the cartridge. The cartridge is preferably not inserted into the nebulizer and/or fluidically connected to the nebulizer until that time, in particular without the actuating mechanism.

According to a second variant of the proposed method, the cartridge is, after components have been fluidically connected or after the components have been mixed, first inserted into the nebulizer, in particular in an unopened state or in the state where it is sealed from the outside or from the environment and/or together with the actuating mechanism. The cartridge is preferably only opened afterwards or in the nebulizer-preferably by actuating or tensioning the nebulizer for the first time—to withdraw a dose of the fluid or to the outside or to the environment and/or fluidically connected to the nebulizer.

According to a third variant of the proposed method, the chambers are fluidically connected to one another only after and/or by the insertion of the cartridge into the nebulizer, or the components are only mixed after and/or by the insertion of the cartridge into the nebulizer. Subsequently, i.e., after mixing the components or after the fluidical connection of the chambers, the cartridge is preferably opened to extract a dose of the fluid, opened toward the outside or the environment and/or fluidically connected to the nebulizer, for example by a first actuation or tensioning of the nebulizer.

In all the variants of the proposed method, the aforementioned actuating mechanism is preferably actuated, in particular manually, in order to fluidically connect the chambers to one another or to mix the components so as to nebulize the fluid.

The fluid or a dose of the fluid can, in particular, be removed by or after the opening of the cartridge.

In the open state or by/after the opening of the cartridge, the cartridge is, in particular, fluidically or pneumatically connected to the environment and/or is no longer sealed against the outside or the environment.

The cartridge is preferably opened by removing the actuating mechanism, by inserting a conveying element into the cartridge, in particular into the closure and/or container of the cartridge, and/or by opening, in particular piercing, a seal of the cartridge, in particular by means of a conveying element of the nebulizer.

The mixing of the components or the connection of the chambers and/or the (complete) actuation of the actuating mechanism is particularly preferably carried out independently and/or before the opening of the cartridge.

It is most particularly preferable if the cartridge is not opened by the (complete) actuation of the actuating mechanism or if the cartridge remains unopened or sealed against the outside or the environment in spite of a (complete) actuation of the actuating mechanism.

In particular, the components are mixed, or the chambers are fluidically connected to one another, or the actuating mechanism is (fully) actuated without opening the cartridge.

Because of this independence, it is possible to open the cartridge without mixing the components or fluidically connecting the chambers to one another or (fully) actuating the actuating mechanism.

As already explained, the components are preferably mixed automatically by the actuation of the actuating mechanism, or one of the components is automatically transferred from one chamber to the other chamber, in particular by a force generated by negative pressure in one of the chambers.

Additionally or alternatively, the cartridge can be aligned after the actuation of the actuating mechanism or after the fluidic connection of the chambers in such a way that the components mix due to gravity, or the first component flows from the first chamber to the second chamber, which contains the second component of the fluid, due to gravity.

In particular, in the first and/or second variant of the proposed method, it is optionally provided that the actuating mechanism is removed from the cartridge after actuation in order to insert the cartridge into the nebulizer. In the first variant of the proposed method, it is preferred to open the cartridge for dispensing a dose of the fluid by removing or detaching the actuating mechanism.

According to a further aspect of the present invention, which can also be realized independently, a liposomal formulation or a liposomally formulated medicament or liposomes is/are produced in the cartridge, in particular in one of the chambers, by actuating the actuating mechanism or by transferring one component from one of the chambers to another of the chambers or by mixing the components.

For this purpose, a lipid solution, in particular an ethanolic lipid solution, as the first component of the medicament is particularly preferably transferred from a first chamber of the cartridge into a second chamber of the cartridge with an aqueous buffer as the second component of the medicament, preferably with the lipid solution and/or the aqueous phase (each) containing at least one active ingredient as already explained. Corresponding advantages are realized in this way.

The above-mentioned aspects and features of the present invention and the aspects and features of the present invention resulting from the claims and the following description can, in principle, be implemented independently from one another but in any combination or sequence as well.

BRIEF DESCRIPTION OF THE DRAWING

Further aspects, advantages, features, and properties of the present invention result from the claims and the following description of preferred embodiments on the basis of the drawings. In the drawings:

FIG. 1 is a schematic section of a known nebulizer in the untensioned state;

FIG. 2 is a schematic section of the nebulizer according to FIG. 1 rotated by 90°, in the tensioned state;

FIG. 3 is a schematic section of a proposed cartridge with two fluidically separated chambers according to a first embodiment;

FIG. 4 is a schematic section of the cartridge according to FIG. 3 with fluidically connected chambers;

FIG. 5 is a schematic section of the cartridge according to FIG. 3 with completely mixed components of the fluid;

FIG. 6 is a schematic section of a portion of the proposed nebulizer with an inserted cartridge according to FIG. 5 in the untensioned state;

FIG. 7 is a schematic section of a proposed cartridge with two chambers fluidically separated from one another according to a second embodiment;

FIG. 8 is a schematic section of the cartridge according to FIG. 7 with fluidically connected chambers;

FIG. 9 is a schematic section of the cartridge according to FIG. 8 rotated by 180°;

FIG. 10 is a schematic section of the cartridge according to FIG. 9 with completely mixed components of the fluid;

FIG. 11 is a schematic section of the cartridge according to FIG. 10 rotated by 180°;

FIG. 12 is a schematic section of a portion of the proposed nebulizer with an inserted cartridge according to FIG. 11 in the tensioned state;

FIG. 13 is a schematic section of a proposed cartridge with two fluidically separated chambers according to a third embodiment;

FIG. 14 is a schematic section of the cartridge according to FIG. 13 with fluidically connected chambers;

FIG. 15 is a schematic section of the cartridge according to FIG. 14 with the actuating mechanism removed; and FIG. 16 is a schematic section of a proposed nebulizer with an inserted cartridge according to FIG. 15.

DETAILED DESCRIPTION

In the drawings, which are only schematic and some of which are not to scale, the same reference numerals are used for identical, equivalent or similar parts and components with which the corresponding or comparable properties and advantages are achieved even if a repeated description is dispensed with.

FIG. 1 and FIG. 2 show a known system with a known dispensing device or a known nebulizer 1 for nebulizing or dispensing a fluid 2, in particular a medicament such as a pharmaceutical composition, a drug or the like, with FIG. 1 showing the dispensing device or the nebulizer 1 in the untensioned state or when a dose of the fluid 2 is being dispensed and FIG. 2 showing the dispensing device or the nebulizer 1 in the tensioned state.

The following statements refer to a nebulizer but also apply accordingly to other dispensing devices such as inhalers, syringes or the like.

The system or the nebulizer 1 is preferably designed to dispense or nebulize the fluid 2 or a dose of the fluid 2.

An aerosol A is preferably formed or released when the fluid 2 is nebulized by means of the nebulizer 1 as indicated in FIG. 1 by dashed lines. The aerosol A can be breathed in or inhaled by a user (not shown).

In general, the nebulizer 1 or the inhalation is used, in particular depending on the symptoms or the illness of the patient or user, at least once a day, preferably several times a day, particularly preferably at certain intervals.

The nebulizer 1 is preferably designed as a mobile or portable inhaler and/or can be operated without electrical energy.

The nebulizer 1 is particularly preferably operated purely mechanically and/or without the use of a propellant gas. However, other design solutions also are possible.

The system or the nebulizer 1 preferably has a cartridge 3, in particular an insertable and/or replaceable cartridge, with the cartridge 3 preferably containing the fluid 2 or forming a reservoir for the fluid 2. In particular, the nebulizer 1 is designed to accommodate the cartridge 3 partially or completely.

Figure 2:
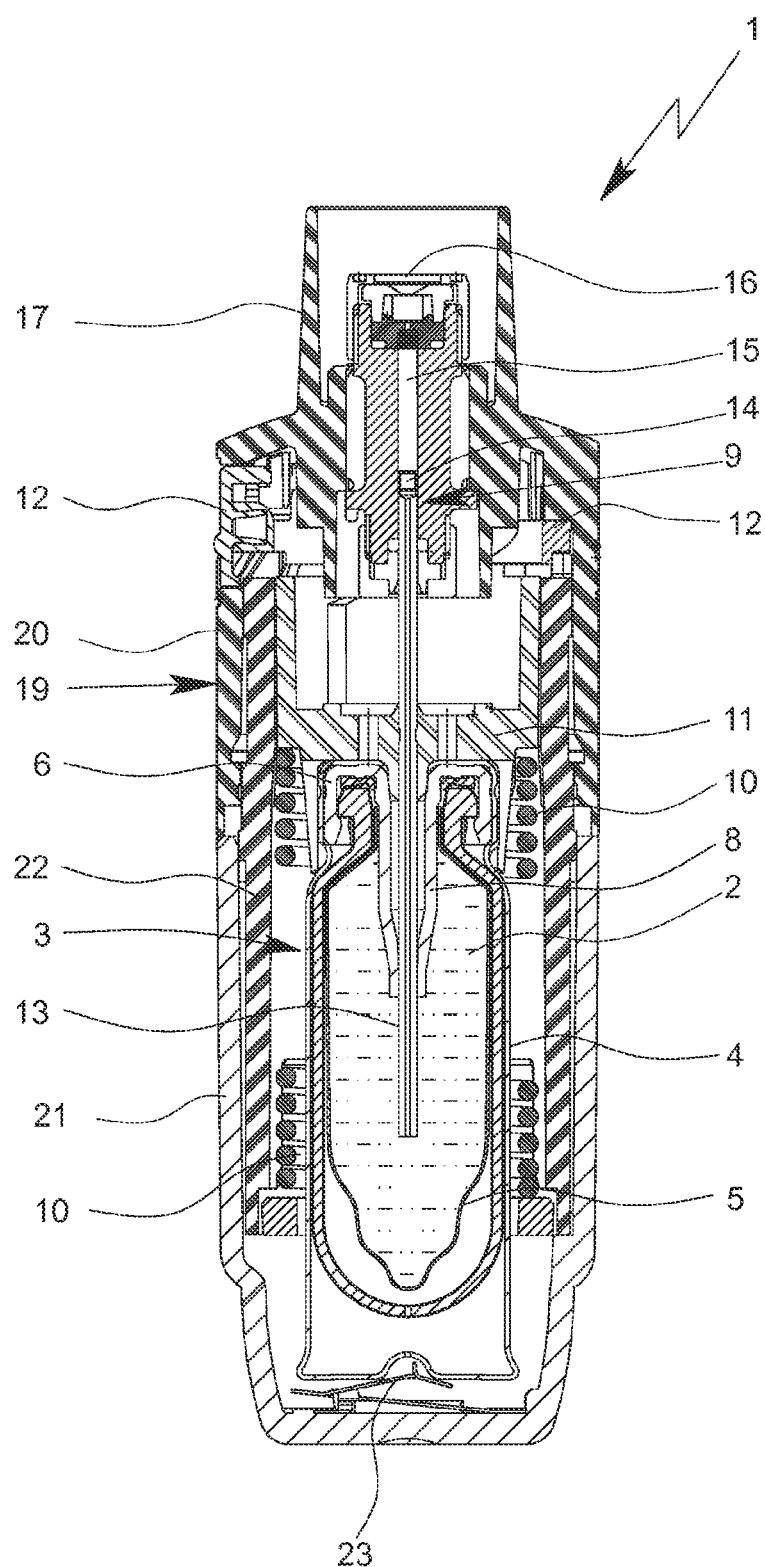

FIG. 1 and FIG. 2 show the known nebulizer 1 with the cartridge 3 being represented schematically.

Figure 5:
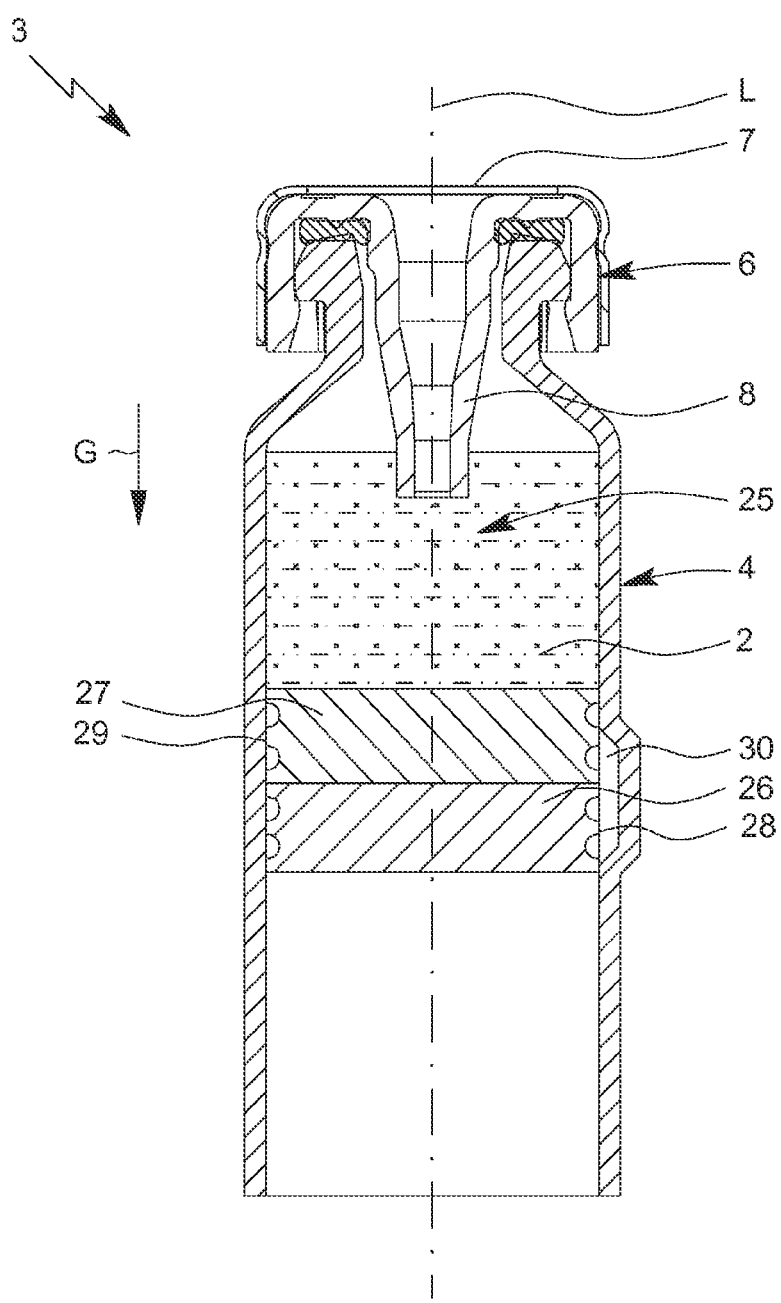
Figure 6:
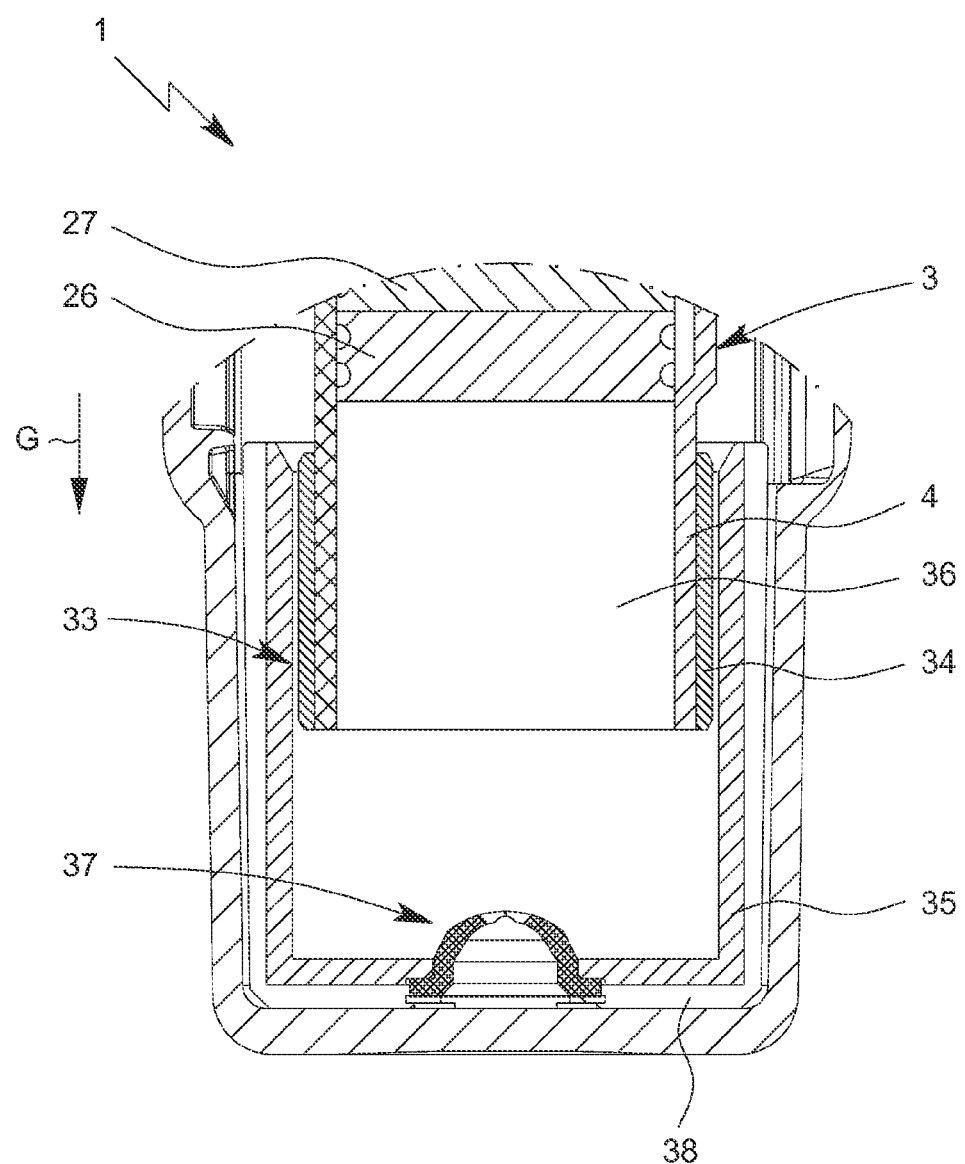
Figure 12:
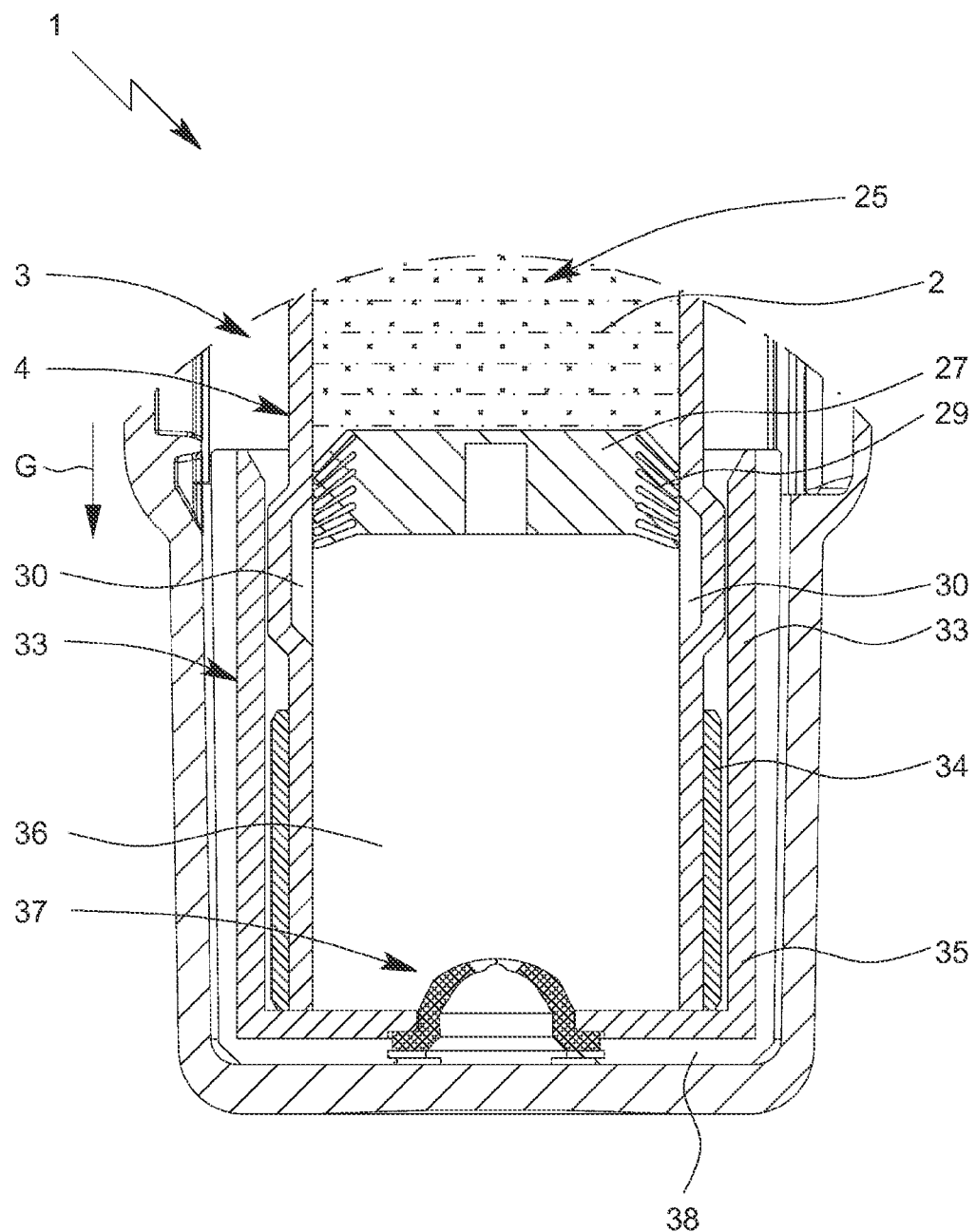
Figure 15:
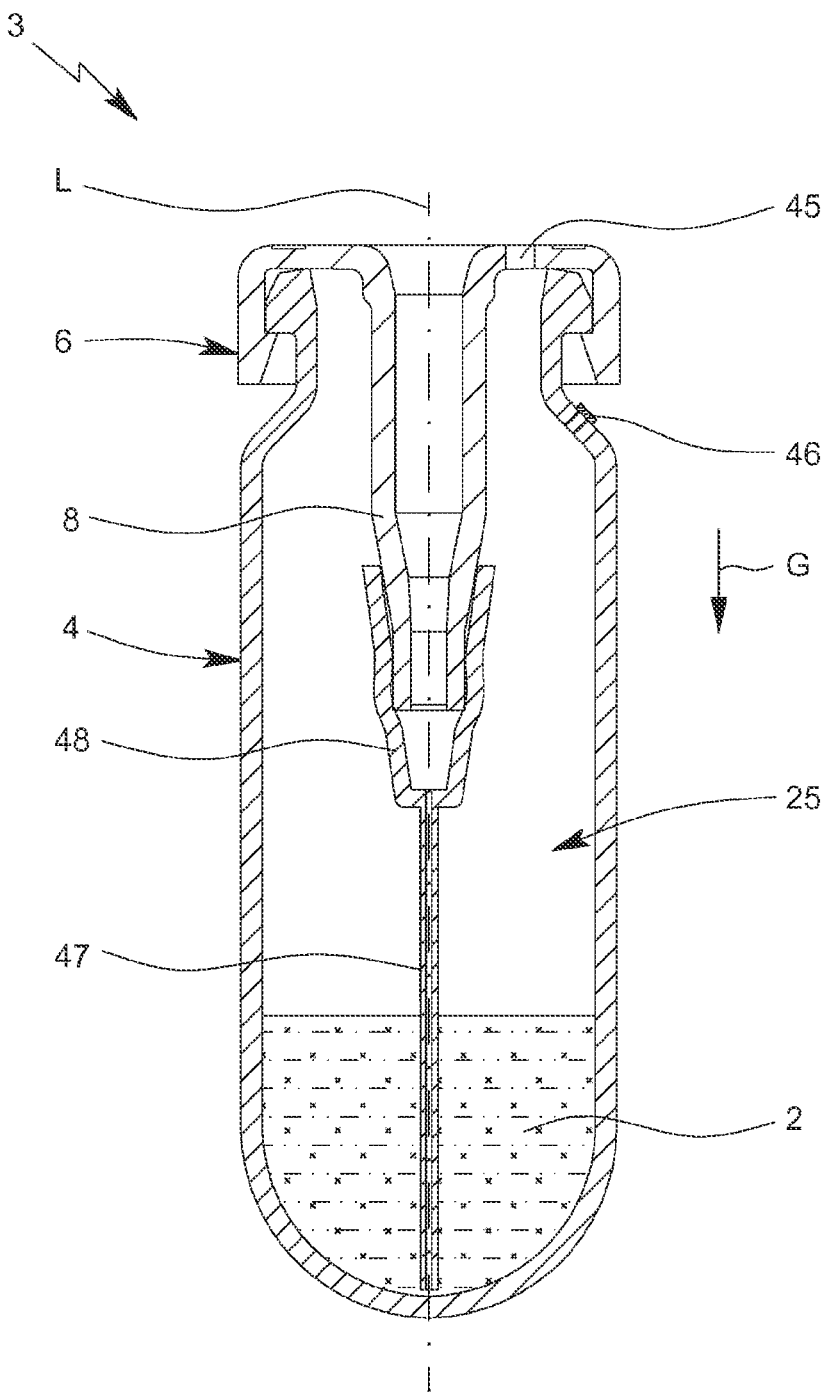
Figure 16:
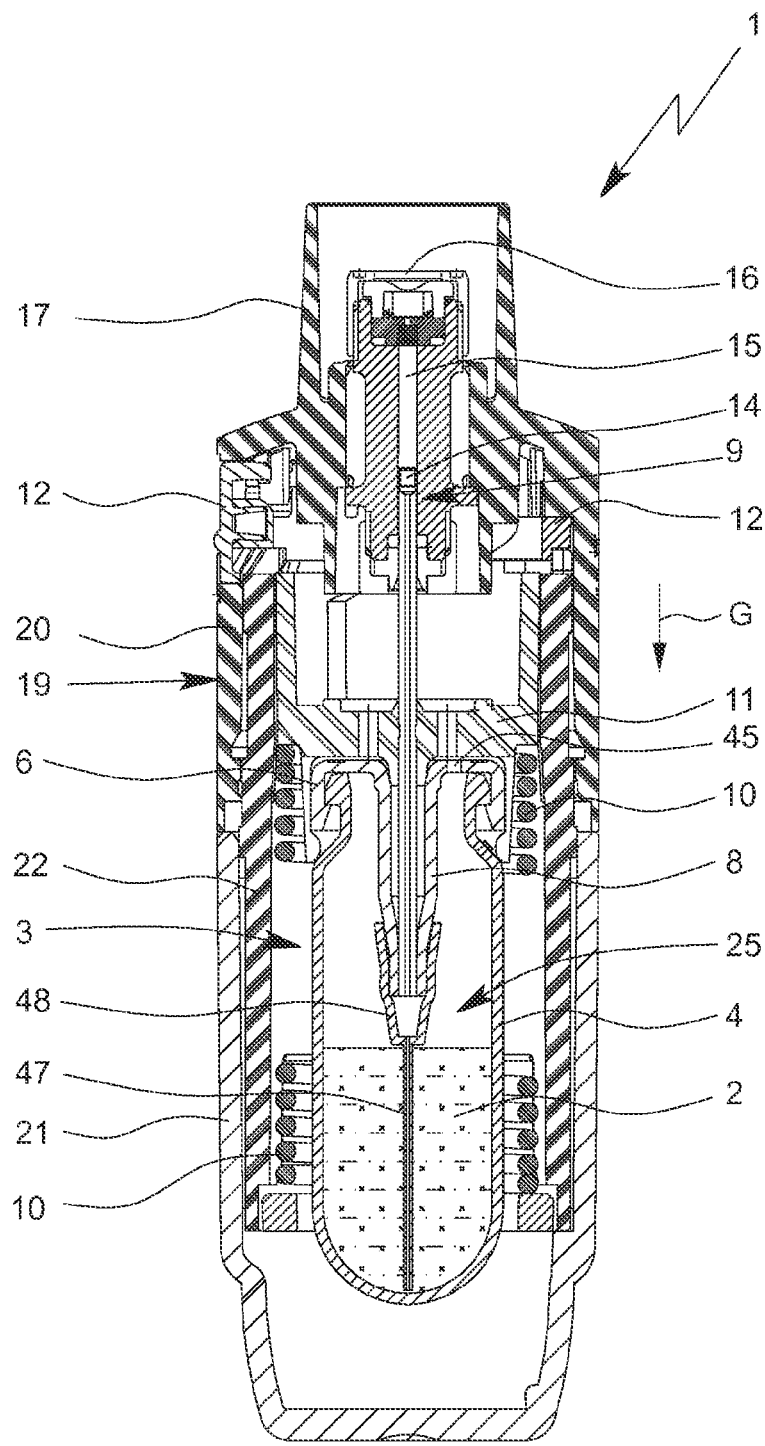

FIGS. 3 to 16 show proposed cartridges 3 or parts thereof, wherein the proposed cartridge 3 can be used with the nebulizer 1 as shown in FIGS. 6, 12 and 16.

The features, properties and aspects described in connection with FIG. 1 and FIG. 2 can preferably be applied to the cartridge 3 or the nebulizer 1 described in connection with FIG. 3 to FIG. 16. In particular, the cartridge 3 described in connection with FIGS. 3 to 16 can have one or more features, properties and aspects of the cartridge 3 described in connection with FIG. 1 and FIG. 2 and/or basically be used in connection with the nebulizer 1 described in FIG. 1 and FIG. 2.

In the following, the known cartridge 3 will first be described on the basis of FIG. 1 and FIG. 2.

The cartridge 3 preferably has a plurality of doses of the fluid 2, in particular in order to provide at least 100, 150 or 200 dispensing units or doses or to allow at least 100, 150 or 200 applications.

The cartridge 3 preferably contains a volume of at least 0.5 ml or at least 4 ml and/or at most 30 ml or 20 ml. The number of doses in the cartridge 3 and/or the total volume of the fluid 2 in the cartridge 3 can vary depending on the fluid 2, the cartridge 3 and/or the required medication. The number of doses or actuations is optionally limited.

The nebulizer 1 preferably has a counter which counts and/or displays the number of actuations of the nebulizer 1, preferably by recording the tensioning of the nebulizer 1. Optionally, the nebulizer 1 or the counting device has a blocking device which blocks the nebulizer 1 from being actuated when a predetermined number of actuations is reached.

The nebulizer 1 is preferably designed to nebulize or emit at least 1 µl or 5 µl and/or at most 100 µl, 50 µl or 20 µl of the fluid 2 when the nebulizer 1 is actuated or used and/or dispenses a dose of the fluid 2.

The nebulizer 1 or the cartridge 3 preferably has a particularly rigid container 4 and/or an optional, preferably flexible or collapsible, bag 5, in particular with the container 4 or the bag 5 containing the fluid 2. The optional bag 5 is preferably arranged within the container 4 and/or held in or by the container 4.

The cartridge 3 is preferably removable or replaceable as disclosed, for example, in WO 2012/162305 A1.

The number of applications of the cartridge 3 or the number of doses of the fluid 2 from said cartridge or from the cartridge 3 inserted in the nebulizer 1 is preferably limited.

The cartridge 3 preferably has a counting device for this purpose, in particular wherein the counting device counts and/or displays the number of actuations of the nebulizer 1 with the same cartridge 3, particularly preferably by recording the tensioning of the nebulizer 1. Optionally, the cartridge 3 or the counting device has a blocking device which blocks an actuation of the nebulizer 1 with the same cartridge 3 when a predetermined number of actuations with the same cartridge 3 is reached. WO 2015/169431 A2 discloses such a counting device, which is preferably assigned to the cartridge 3.

Optionally, the number of cartridges 3 that can be used by means of the same nebulizer 1 is limited, for example to a maximum number of four, five or six cartridges 3, preferably by means of the already mentioned counting device(s) or blocking device(s). WO 2012/162305 A1 discloses a restriction on the number of cartridges 3 that can be used with the same nebulizer 1.

The cartridge 3, in particular the container 4, is preferably elongated, rigid and/or at least substantially cylindrical or designed as a hollow cylinder. However, other design solutions are also possible, in particular those in which the cartridge 3 or the container 4 is at least substantially or at least partially spherical.

The container 4 is preferably open at one axial end, and/or the container 4 has an opening for the removal of the fluid 2 at one end or at an axial end.

The nebulizer 1 is preferably openable, and/or the cartridge 3 can be inserted into or replaced in the nebulizer 1 by opening the nebulizer 1, preferably from below.

The cartridge 3 is preferably closed and/or sealed toward the outside or the environment, in particular in a gastight and/or liquid-tight manner, at least in the delivery state.

The cartridge 3 preferably has a closure 6, preferably with the closure 6 being connected to the container 4 in a form-fit, force-fit and/or cohesive manner and/or axially closing the container 4.

In particular, the closure 6 is designed to close or seal the container 4 or the bag 5, in particular axially or at the open end of the container 4, in particular in a gastight and/or liquid-tight manner.

The end of the container 4 on which the closure 6 is arranged or the end of the cartridge 3 which comprises the closure 6 is referred to below as the "upper end". Correspondingly, the end of the cartridge 3 or the container 4 (axially) opposite the closure 6 is the "lower end". This preferably corresponds to the preferred orientation of the cartridge 3 in the nebulizer 1 during use. However, it is preferably also possible to use the nebulizer 1 or the cartridge 3 in other orientations.

The closure 6 is preferably designed to fluidically connect the container 4 to the nebulizer 1, in particular when the cartridge 3 is or is being inserted into the nebulizer 1.

The cartridge 3, in particular the closure 6, preferably has a seal 7, in particular an openable, preferably pierceable seal, and/or a connection 8, in particular a funnel-shaped and/or conical connection.

Figure 3:
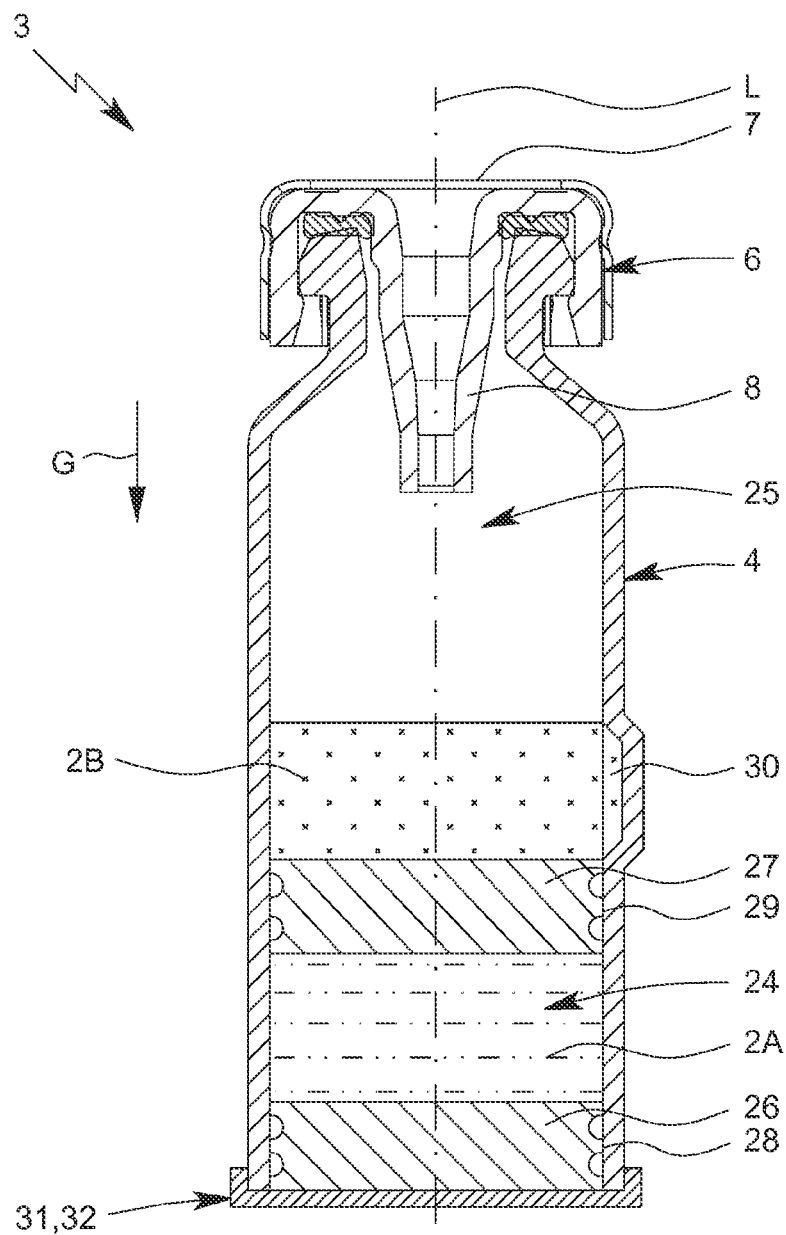

The seal 7 is shown, for example, in FIG. 3 in which the proposed cartridge 3 according to a first embodiment is shown in the closed state or in the delivery state.

The seal 7 is preferably designed as a seal or barrier and/or seals the container 4, bag 5 and/or the connection 8, in particular axially and preferably at least before the cartridge 3 is inserted into the nebulizer 1 or before the seal 7 is pierced. In particular, the seal 7 offers protection against evaporation.

The seal 7 is preferably designed as a film, membrane, diaphragm, septum or the like.

The known nebulizer 1 according to FIG. 1 and FIG. 2 preferably has a pump 9, in particular a mechanical pump, with the pump 9 preferably being designed as a dispensing or pressure mechanism. In particular, the pump 9 is designed to suck the fluid 2 or a dose of the fluid 2 from the container 4 or the bag 5, put it under pressure, convey it upwards within the nebulizer 1 and/or nebulize or dispense it, wherein preferably the volume of the dose of the fluid 2 delivered by means of the pump 9 is predefined and optionally adaptable.

Preferably, the fluid 2 or a dose of the fluid 2 can be removed or sucked out of the cartridge 3, in particular the container 4 or bag 5, by means of the pump 9 when the nebulizer 1 is tensioned or loaded. The removed fluid 2 or the dose of the fluid 2 can then be dispensed, in particular pressurized and/or nebulized, in particular by means of the mechanical energy that was stored during the tensioning or charging of the nebulizer 1, as will be explained below.

The nebulizer 1 preferably has an energy storage which is charged or tensioned during the charging or tensioning of the nebulizer 1. The energy stored in the energy storage is used to dispense or nebulize the fluid 2 or a dose of the fluid 2 that was removed during the tensioning or loading of the cartridge 3, in particular the container 4 or bag 5. The normal use of the nebulizer 1 consequently includes a loading or tensioning process and a (subsequent) dispensing or nebulizing process.

The nebulizer 1 preferably has a drive spring 10, with the drive spring 10 preferably forming the energy storage or part of the energy storage. The drive spring 10 is particularly preferably tensionable, particularly preferably compressible, in particular during the loading or tensioning process of the nebulizer 1, preferably in order to store energy for the (subsequent) dispensing of the fluid 2 or a dose of the fluid 2 or for the dispensing or nebulizing process.

The nebulizer 1 preferably has a locking element 12, in particular a ring-shaped locking element, with the locking element 12 in particular being designed to block or prevent an—accidental or immediate-relaxation of the tensioned drive spring 10. The locking element 12 is preferably provided with a button, in particular accessible from the outside, for a preferably manual actuation. In particular, by actuating the locking element 12 or the button thereof, the drive spring 10 can be released or relaxed, in particular in such a way that the dispensing or nebulizing process is carried out.

The nebulizer 1, in particular the pump 9, preferably has a holder 11, with the holder 11 preferably being designed to hold the cartridge 3, in particular the closure 6 of the cartridge 3, and/or the drive spring 10 assigned to the holder 11, and/or the part of the drive spring 10 assigned to the holder 11, and/or the locking element 12, in particular in a form-fitting and/or force-fitting manner.

The holder 11 is preferably designed to hold the cartridge 3 in a releasable manner, in particular in such a way that the cartridge 3 can be removed or pulled out or replaced.

The locking element 12 is preferably designed to secure or lock the holder 11 against an axial movement, in particular in a form-fitting and/or force-fitting manner. In particular, the locking element 12 can be operated manually in order to release the holder 11 and thus the drive spring 10.

The nebulizer 1, in particular the pump 9, preferably has a conveying element 13, a one-way valve 14, a pressure chamber 15 and/or a nozzle 16 for nebulizing the fluid 2 or a dose of the fluid 2.

The conveying element 13 is preferably designed as an elongated hollow cylinder, in particular as a needle, cannula or the like, and/or the conveying element 13 has a tapering or sharp end, in particular in order to sever the seal 7. The conveying element 13 is preferably rigid and/or made of metal, in particular of stainless steel.

The cartridge 3, which is preferably completely inserted, is preferably fixed or held in the nebulizer 1 by means of the holder 11 in such a way that the conveying element 13 (fluidically) connects the cartridge 3, in particular the container 4 or the bag 5, to the nebulizer 1, in particular the pump 9.

Particularly preferably, the conveying element 13 penetrates the seal 7, and/or the conveying element 13 protrudes at least partially into the cartridge 3, in particular into the container 4 or the bag 5, when the cartridge 3 is or is being inserted into the nebulizer 1.

In particular, the cartridge 3, particularly preferably the container 4 or the bag 5, is made openable or fluidically connectable to the nebulizer 1 or the pump 9 by inserting the conveying element 13 into the cartridge 3, in particular into the container 4 or the bag 5 and/or into the closure 6 or connection 8, and/or by piercing the seal 7 by means of the conveying element 13.

If the drive spring 10 is tensioned, in particular compressed, during the tensioning process of the nebulizer 1, the holder 11, the cartridge 3 and the conveying element 13 are preferably moved together in a downward direction or in the direction of the bottom of the cartridge 3.

By moving the conveying element 13 downward or in the direction of the bottom of the cartridge 3, the volume of the pressure chamber 15 of the pump 9 is increased, or the pressure within the pressure chamber 15 is reduced, in particular such that the fluid 2 from the cartridge 3, in particular the container 4 or the bag 5, is sucked into the pump 9 or the pressure chamber 15 by means of the conveying element 13, in particular via the one-way valve 14.

At the end of the tensioning process, the holder 11 preferably engages with the locking element 12, and/or the holder 11 rests against the locking element 12 at the end of the tensioning process, in particular in such a way that the drive spring 10 remains tensioned. In this state, the nebulizer 1 is tensioned or activated and therefore ready for the dispensing process.

The subsequent dispensing process is initiated by actuating the nebulizer 1, in particular the locking element 12. In particular, by actuating the nebulizer 1, in particular the locking element 12, the holder 11 or the drive spring 10 is released, in particular in such a way that the drive spring 10 can relax at least partially.

As a result of the relaxation of the drive spring 10 during the dispensing process, i.e., after actuation of the nebulizer 1 or the locking element 12, the conveying element 13 moves, preferably together with the now closed one-way valve 14, back in the direction of the pressure chamber 15, in FIG. 1 and FIG. 2 upwards, and in this way reduces the volume of the pressure chamber 15. Due to the one-way valve 14 being closed during the dispensing process, the fluid 2 introduced into the pressure chamber 15 or the dose of the fluid 2 introduced there is pressurized. The one-way valve 14 consequently preferably serves as a pressure tappet or plunger during the dispensing process.

The pressure generated in this way forces the fluid 2 or the extracted dose of the fluid 2 through the nozzle 16, as a result of which the nebulization of the fluid 2 or the dose of the fluid 2 takes place or the aerosol A is formed, as indicated in FIG. 1 by dashed lines.

A pressure of at least 5 MPa or 10 MPa and/or at most 300 MPa or 250 MPa, in particular at most 100 MPa or 50 MPa, particularly preferably at least substantially 30 MPa, is preferably generated by the pump 9, in particular the drive spring 10.

In this way, the fluid 2 is nebulized to form aerosol A with the (average) aerodynamic diameter of the droplets of aerosol A preferably being less than 20 μm, preferably at least 3 μm and/or at most 10 μm.

The spray jet of the aerosol A generated in this way preferably has a (spray) angle between 20° and 160°, particularly preferably between 80° and 100°.

The stated values also apply in particular to the proposed nebulizer 1.

A user or patient can inhale the aerosol A generated in this way preferably while air is simultaneously sucked in via a mouthpiece 17, in particular through at least one optionally provided ventilation opening 18.

The nebulizer 1 preferably has a housing 19 for accommodating the cartridge 3, with the housing 19 preferably being designed in multiple parts and/or having an upper housing part 20, a lower housing part 21 and/or an inner housing part 22.

The inner housing part 22 and/or the lower housing part 21 are/is preferably rotatable relative to the upper housing part 20. In particular, the lower housing part 21 is connected to the inner housing part 22 and/or is slipped onto the inner housing part 22, in particular via a corresponding holding element of the inner housing part 22, in a manually operable or releasable manner.

The housing 19 is preferably openable, in particular at the bottom, in particular in order to insert or replace the cartridge 3 in the nebulizer 1 or the housing 19, in particular from below. In particular, the lower housing part 21 can be removed from the nebulizer 1, in particular from the inner housing part 22, in order to insert or replace the cartridge 3.

The cartridge 3 is preferably inserted into the nebulizer 1 and opened in the housing 19 or fluidically connected to the nebulizer 1, in particular the pump 9, preferably before the housing 19 is closed and/or the lower housing part 21 is connected to the inner housing part 22 or the upper housing part 20. In particular, the cartridge 3 is opened by inserting the cartridge 3 into the nebulizer 1 or into the housing 19 and/or is fluidically connected to the nebulizer 1, in particular the pump 9. Alternatively, the cartridge 3 can be opened and/or fluidically connected to the nebulizer 1, in particular the pump 9, by (completely) closing the housing 19 or (completely) connecting the lower housing part 21 to the upper housing part 20 or the inner housing part 22, particularly preferably automatically or at least substantially simultaneously. Alternatively, the cartridge 3 is only opened or fluidically connected to the nebulizer 1 or the pump 9 when the nebulizer 1 is tensioned by the inserted cartridge 3 for the first time.

The nebulizer 1 or the drive spring 10 can preferably be manually operated, activated or tensioned, in particular by activating or rotating the lower housing part 21. However, other solutions are also possible in this regard.

The lower housing part 21 can preferably be actuated together with the inner housing part 22, in particular is rotatable relative to the upper housing part 20, in order to tension the nebulizer 1.

The inner housing part 22 preferably serves as a drive and/or is preferably designed to convert the rotational movement of the lower housing part 21 into an axial or lifting movement of the holder 11 or the cartridge 3. In particular, the drive spring 10 is tensioned, particularly preferably compressed in the axial direction, by means of the inner housing part 22.

The lower housing part 21 preferably forms a bottom of the nebulizer 1 and/or accommodates the cartridge 3 at least partially axially.

During the tensioning process, the cartridge 3 and the holder 11 are preferably moved axially in the downward direction or in the direction of the lower housing part 21 until the cartridge 3 reaches an end position/tensioning position as shown in FIG. 2.

In the activated or tensioned state or in the end position, the drive spring 10 is under tension, preferably with the drive spring 10 being secured or prevented from relaxing by means of the locking element 12, as already explained.

During the dispensing process, the cartridge 3 is brought back into its original or non-tensioned position or rest position by the (force of the) drive spring 10, as shown in FIG. 1. The cartridge 3 consequently performs an axial or lifting movement in the nebulizer 1 during the tensioning and dispensing process.

The nebulizer 1, in particular the housing 19, particularly preferably the lower housing part 21, preferably has a ventilation means 23, such as a piercing element, preferably with the ventilation means 23 being designed to open or pierce the cartridge 3, in particular the container 4, when the cartridge 3 is connected to the ventilation means 23 for the first time or comes into contact therewith. In this way, air can get into the cartridge 3, in particular into the container 4, and a pressure equalization can take place when the fluid 2 or a dose of the fluid 2 is removed from the cartridge 3.

As already explained, however, other design solutions are also possible, in particular solutions in which the optional bag 5 is omitted. The ventilation means 23 can then optionally be omitted as well. Such embodiments without a bag 5 are described below on the basis of FIGS. 3 to 16.

The cartridge 3 according to the various embodiments shown in FIGS. 3 to 16 is designed as a multi-chamber cartridge, in particular a double-chamber cartridge, and/or preferably has a plurality or at least two chambers 24, 25, preferably with the chambers 24, 25 being fluidically separated from one another, spaced apart from one another and/or closed in each case, at least in the delivery state of the cartridge 3.

The fluid 2 is preferably composed or can be composed of a plurality of components or parts 2A, 2B.

The components 2A, 2B of the fluid 2 are, at least in the delivery state of the cartridge 3, preferably stored or contained in the cartridge 3, in particular in the container 4, in such a way that they are fluidically separated from one another or located at a distance from one another, in particular to increase the shelf life of the fluid 2. In particular, the fluid 2 is only produced or prepared for delivery or nebulization when the individual components 2A, 2B are brought into contact or fluidically connected and/or mixed.

The chambers 24, 25 preferably each contain at least one of the components 2A, 2B of the fluid 2. In particular, the first chamber 24 contains the first component 2A, and/or the second chamber 25 contains the second component 2B.

In the embodiments shown, the cartridge 3 has two chambers 24, 25. However, design solutions are also possible in which the cartridge 3 has more than two chambers, for example three or four chambers, in particular to store more than two components, for example three or four components, of the fluid 2 separately from one another.

As already explained at the outset, the components 2A, 2B can be solid or liquid. In particular, one component of the components 2A, 2B, preferably the second component 2B, can be solid and another component of the components 2A, 2B, preferably the first component 2A, can be liquid. However, it is also possible for both or all the components 2A, 2B to be liquid.

The cartridge 3 or the container 4 is preferably elongated and/or at least substantially cylindrical, in particular formed as an elongated hollow cylinder. In particular, the cartridge 3 or the container 4 has a longitudinal axis L, with the cartridge 3 or the container 4 preferably being at least substantially rotationally or cylinder-symmetrical about the longitudinal axis L and/or the longitudinal axis L, forming a rotational axis of the cartridge 3 or the container 4. The longitudinal axis L preferably runs centrally through the cartridge 3 or the container 4.

The chambers 24, 25 are preferably formed in or through the container 4. In particular, the container 4 or the wall of the container 4 delimits the chambers 24, 25 radially or laterally. However, other solutions are also possible in this regard.

The chambers 24, 25 are preferably arranged one above the other, as shown in FIG. 3. In particular, the longitudinal axis L of the cartridge 3 runs at least substantially centrally both through the first chamber 24 and through the second chamber 25, and/or the chambers 24, 25 are axially spaced from one another.

The second chamber 25 is preferably arranged between the first chamber 24 and the closure 6, and/or the second chamber 25 is arranged closer to the closure 6 of the cartridge 3 than the first chamber 24.

In principle, however, design solutions are also possible in which the chambers 24, 25 are arranged next to one another and/or at least substantially at the same height in the cartridge 3 or radially offset from one another and/or (differently) spaced from the longitudinal axis L.

The chambers 24, 25 are preferably at least in the delivery state of the cartridge 3 or are temporarily fluidically separated from one another and/or each closed, preferably in a liquid-tight and/or gastight manner, in particular in such a way that the components 2A, 2B of the fluid 2 do not mix or cannot come into contact with one another, and/or the components 2A, 2B are fluidically separated from one another or stored separately and/or at a distance from one another in the cartridge 3.

The volumes of the chambers 24, 25 are preferably different. The volume of the second chamber 25 is particularly preferably greater than the volume of the first chamber 24, preferably by at least 1.2 or 1.5 times, particularly preferably at least 2.0 or 2.5 times. In particular, the second chamber 25 is designed to accommodate the (entire) volume of the first chamber 24, as will be explained in more detail below.

In the delivery state of the cartridge 3, the first chamber 24 is preferably at least substantially completely filled with the first component 2A, and/or at least 90% of the volume of the first chamber 24 is taken up by the first component 2A.

In the delivery state of the cartridge 3, the second chamber 25 is preferably only partially filled with the second component 2B, and/or the second component 2B takes up at most 80% or 70%, in particular at most 60% or 50%, of the volume of the second chamber 25. In the delivery state of the cartridge 3, the second chamber 25 particularly preferably has sufficient space or capacity to preferably accommodate all of the first component 2A but at least 80% or 90% of the first component 2A.

Figure 7:
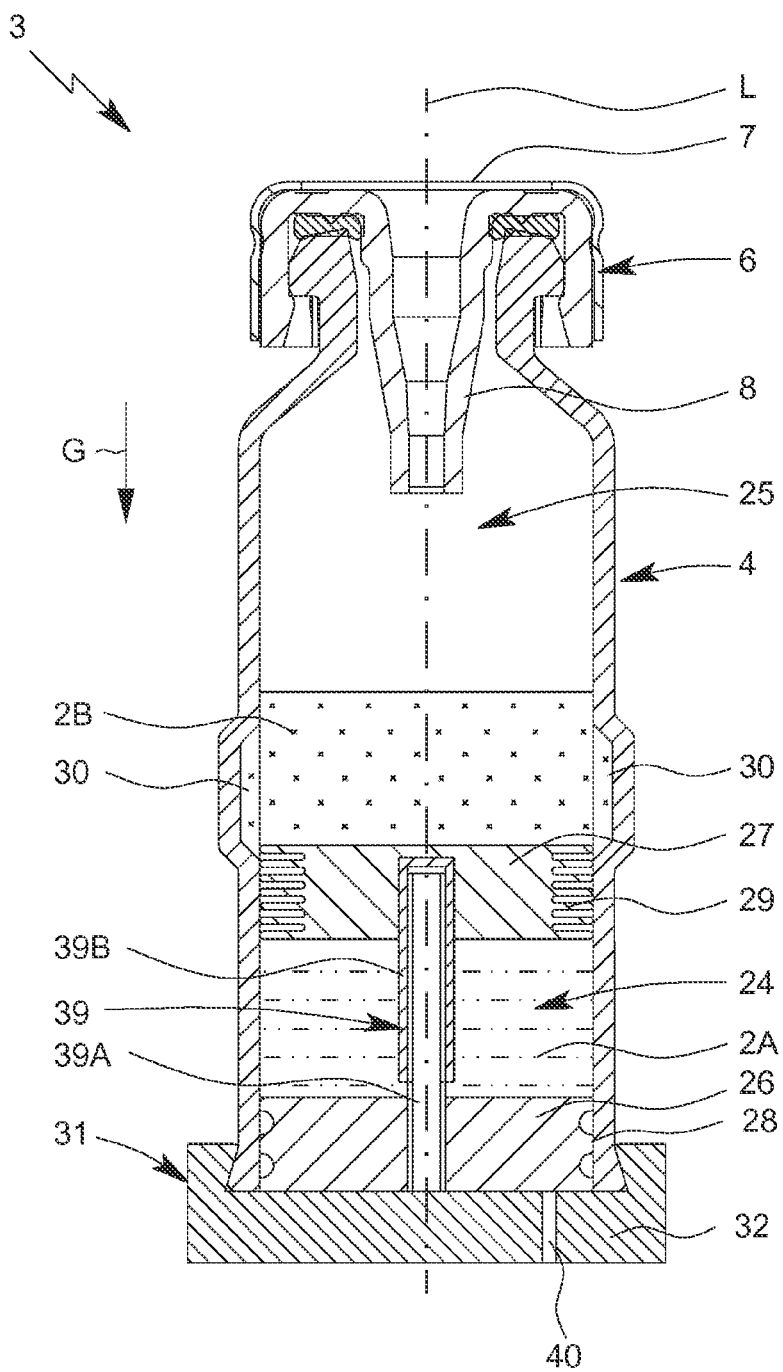
Figure 13:
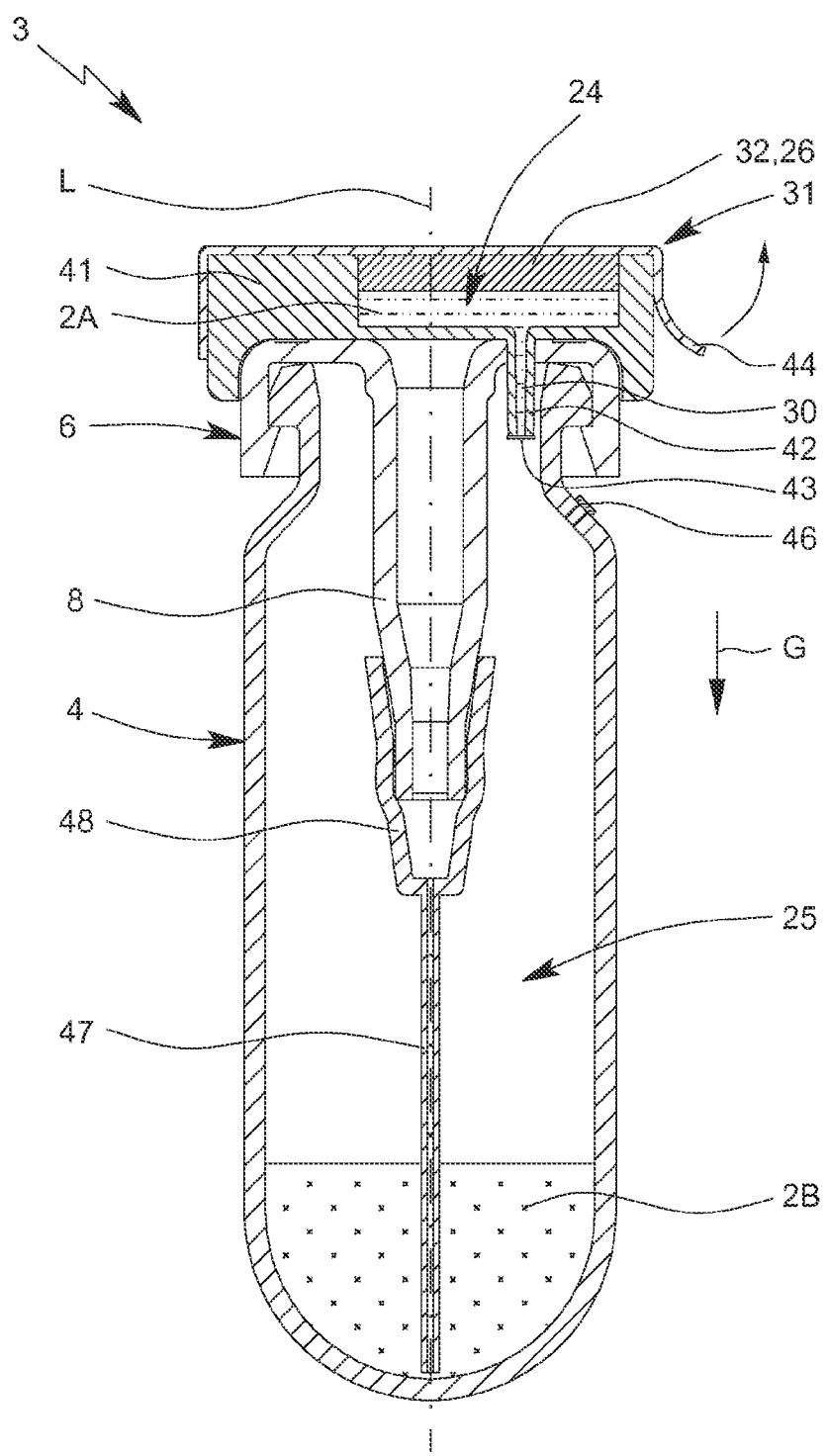

The delivery state of the cartridge 3 is preferably the state of the cartridge 3 in which the cartridge 3 is unopened or sealed against the outside or against the environment and/or is not actuated, as shown in FIGS. 3, 7 and 13. In particular, the volume of the first chamber 24 and/or the volume of the second chamber 25 in the delivery state of the cartridge 3 is at its maximum or the maximum volume that the first chamber 24 or second chamber 25 can accommodate.

At least one of the chambers 24, 25, in particular both the first chamber 24 and the second chamber 25, can preferably be reduced in size.

The cartridge 3 preferably has at least one movable or displaceable plunger 26, with the volume of the first chamber 24 preferably being able to be reduced by moving or displacing the plunger 26.

In the first embodiment shown in FIGS. 3 to 6 and in the second embodiment shown in FIGS. 7 to 12, the cartridge 3, in particular the container 4, has a plurality of plungers 26, 27 or a first plunger 26 and a second plunger 27, with the plungers 26, 27 preferably being axially movable or displaceable in the cartridge 3 or in the container 4 and/or with the cartridge 3, in particular the container 4 and/or the closure 6, having or forming a cylinder for the plungers 26, 27.

The plungers 26, 27 are preferably guided laterally or radially from the container 4, and/or the plungers 26, 27 lie laterally or radially, in particular directly, on the container 4 or the wall of the container 4.

The plungers 26, 27 are preferably movable or displaceable along the longitudinal axis L and/or axially spaced from one another or arranged one above the other.

The second plunger 27 is preferably arranged between the closure 6 and the first plunger 26 and/or closer to the closure 6 than the first plunger 26.

The plungers 26, 27 preferably delimit the chambers 24, 25 axially, and/or the plungers 26, 27 (each) form at least one wall of the chambers 24, 25.

The first plunger 26 preferably delimits the first chamber 24 in the downward direction and/or the first plunger 26 forms a bottom of the first chamber 24. The second plunger 27 preferably delimits the first chamber 24 at the top, and/or the second chamber 25 at the bottom and/or the second plunger 27 forms a bottom of the second chamber 25.

The second plunger 27 particularly preferably separates the first chamber 24 from the second chamber 25, and/or the second plunger 27 seals the first chamber 24 against the second chamber 25, at least in the delivery state of the cartridge 3.

The plungers 26, 27 are preferably at least substantially identical in construction. In particular, the geometry of the first plunger 26 corresponds at least substantially to the geometry of the second plunger 27. The plungers 26, 27 are most particularly preferably made from the same material, and/or the plungers 26, 27 have at least substantially the same height and/or at least substantially the same diameter. However, other solutions are possible in this regard as well, as will be explained below with reference to FIG. 7 to FIG. 12.

The plungers 26, 27 are preferably guided in a sealing manner in the cartridge 3, in particular in the container 4, in particular in such a way that no fluid 2 can pass from one side of the plungers 26, 27 to the other, at least in the delivery state of the cartridge 3.

The plungers 26, 27 preferably rest radially or in a sealing manner and particularly in a direct manner on the inner wall of the cartridge 3, in particular the container 4. In particular, the outer diameter of the plungers 26, 27 corresponds at least substantially to the inner diameter of the cartridge 3 or the container 4. It is preferred that the outer diameter of the plungers 26, 27 is slightly larger than the inner diameter of the cartridge 3 or the container 4, preferably by at least 0.1 mm or 0.3 mm and/or at most by 1 mm or 0.8 mm, in particular in such a way that the plungers 26, 27 are pressed into the cartridge 3 or the container 4 and/or come in contact with the inner wall of the cartridge 3 or the container 4 in a sealing manner.

The plungers 26, 27 preferably each have a plunger seal 28 and 29, with the plunger seals 28, 29 preferably being designed to seal the region between the plungers 26, 27 and the wall or the inner wall of the cartridge 3 or the container 4.

In the embodiment shown, the plunger seals 28, 29 are formed by a plurality of circumferential, radial projections.

As already explained, the second plunger 27, in particular, is designed to fluidically separate the chambers 24, 25 from one another, at least in the delivery state of the cartridge 3.

The chambers 24, 25 can preferably be fluidically connected to one another by moving or displacing the first plunger 26 and/or the second plunger 27, in particular such that the first component 2A and the second component 2B can come into contact or be mixed with one another.

In the embodiment shown, a fluidical connection between the chambers 24, 25 can be established by displacing the second plunger 27 in the direction of the closure 6 or in the upward direction.

The cartridge 3, in particular the container 4, preferably has a fluid connection 30, or the cartridge 3, in particular the container 4, forms a fluid connection 30, in particular with the fluid connection 30 being designed to fluidically connect the chambers 24, 25 to one another and/or to allow a transfer of the first component 2A from the first chamber 24 to the second chamber 25.

Figure 4:
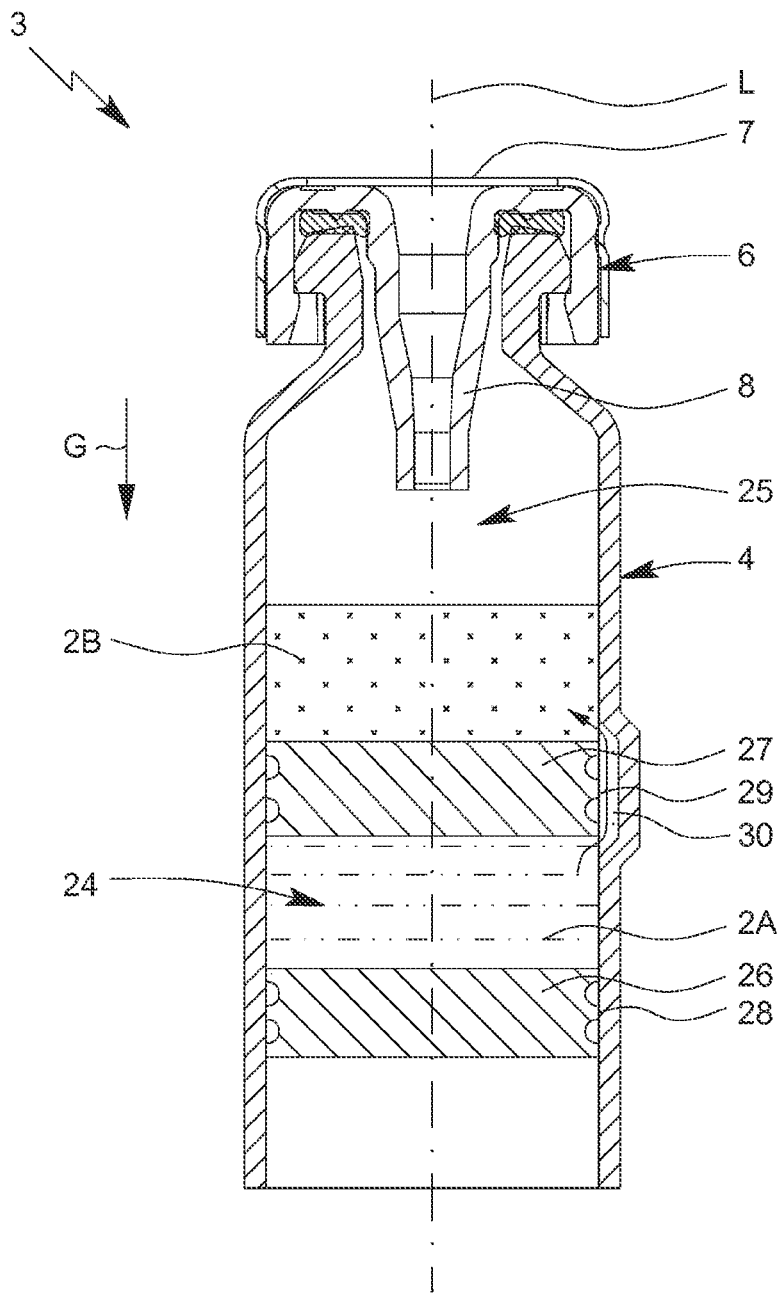

The fluid connection 30 can preferably be released by displacing the first plunger 26 and/or the second plunger 27, in the first embodiment by displacing the second plunger 27, in particular in such a way that the chambers 24, 25 are fluidically connected to one another, as shown in FIG. 4.

The fluid connection 30 is preferably elongated and/or designed as a channel or a bypass.

The fluid connection 30 is preferably arranged eccentrically and/or at a distance from the longitudinal axis L, and/or the fluid connection 30 runs at least substantially parallel to the longitudinal axis L of the cartridge 3.

In particular, the fluid connection 30 is formed by the container 4 or the wall of the container 4, most particularly preferably by a (radial) protuberance of the container 4 or a (local) cross-sectional enlargement of the container 4.

The cross section of the cartridge 3 or the container 4 is locally enlarged to form the fluid connection 30, and/or the cartridge 3 or the container 4 has a portion in which the inner diameter of the cartridge 3 or the container 4 is greater than the outer diameter of the first plunger 26 and/or second plunger 27, preferably by at least 0.5 mm or 1 mm, in particular such that the first plunger 26 and/or the second plunger 27 does not radially rest on the cartridge 3 or the container 4 over the entire circumference of the plunger 26 or 27, at least at the height of the portion or the fluid connection 30.

The fluid connection 30 preferably has a maximum diameter or a maximum width of at least 0.5 mm or 1 mm and/or is at the most 5 mm or 4 mm, or the inner diameter of the cartridge 3 or the container 4 is enlarged by these values at the point of the fluid connection 30.

The fluid connection 30 preferably has a longitudinal extension which is longer than the height of the first or second plunger 26, 27. The fluid connection 30 preferably has a longitudinal extension of at least 3 mm or 4 mm, particularly preferably of at least 6 mm or 8 mm, and/or at most 20 mm or 15 mm, particularly preferably at most 10 mm, and/or the fluid connection 30 is at least 1 mm or 2 mm, preferably at least 5 mm or 6 mm, longer than the height of the first or second plunger 26, 27.

As already explained, the fluid connection 30 is preferably only formed locally, or the fluid connection 30 preferably does not extend over the entire length or over the entire circumference of the cartridge 3 or the container 4. However, design solutions are also possible in which the cartridge 3 or the container 4 has a plurality of fluid connections 30, in particular distributed over the circumference of the container 4, as will be explained below with reference to the second embodiment.

The cartridge 3 preferably has an actuating mechanism 31, in particular with the chambers 24, 25 being able to be fluidically connected to one another by actuating the actuating mechanism 31 and/or the plunger or plungers 26, 27 in the cartridge 3 or in the container 4 being displaceable by actuating the actuating mechanism 31. In particular, the components 2A, 2B can be brought into contact or mixed by actuating the actuating mechanism 31.

The actuating mechanism 31 preferably has an actuating element 32, in particular with the actuating mechanism 31 or the cartridge 3 being actuated by an actuation of the actuating element 32.

The actuating mechanism 31 or the actuating element 32 is preferably rigid.

The actuating mechanism 31 or the actuating element 32 is particularly preferably designed in the form of a plate, a circle, a cap and/or a cylinder and/or formed as a cap, a cylinder and/or a top part.

The actuating mechanism 31 is connected to the cartridge 3, in particular the container 4 or the closure 6, in particular in a form-fit, force-fit and/or cohesive manner, particularly preferably by a screwing or locking mechanism.

The actuating mechanism 31 or the actuating element 32 is preferably plugged into or screwed onto the cartridge 3, in particular the container 4 or closure 6, or is inserted into the cartridge 3, in particular the container 4 or closure 6.

In the embodiments shown, the actuating mechanism 31 or the actuating element 32 is plugged into or screwed onto the cartridge 3, in particular the container 4 or closure 6, or the actuating mechanism 31 or the actuating element 32 engages around the cartridge 3, in particular the container 4 or closure 6.

The maximum outer diameter of the actuating mechanism 31 or the actuating element 32 is particularly preferably greater than the maximum outer diameter of the part of the cartridge 3, in particular of the container 4 or closure 6, to which the actuating mechanism 31 or the actuating element 32 is connected. However, solutions are also possible in which the actuating mechanism 31 or the actuating element 32 is inserted into or screwed onto or plugged into the cartridge 3, in particular the container 4 or closure 6.

The actuating mechanism 31 is preferably arranged at an axial end of the cartridge 3, in particular the container 4 or the closure 6, and/or closes the cartridge 3, in particular the container 4 or the closure 6, preferably in an axial manner. In particular, the actuating mechanism 31 forms an axial end, a bottom and/or a cover of the cartridge 3.

In the first and second embodiment, the actuating mechanism 31 is preferably arranged at the end of the cartridge 3 or the container 4 (axially) opposite the closure 6. In particular, the actuating mechanism 31 then forms a base of the cartridge 3.

In the third embodiment, the actuating mechanism 31 is preferably arranged on the closure 6 or the (axial) end of the cartridge 3 comprising the closure 6. In particular, the actuating mechanism 31 then forms a cover of the cartridge 3.

In the first and second embodiment, the actuating mechanism 31 is preferably connected to the container 4 or attached to the container 4. However, solutions are also possible in which the actuating mechanism 31 is connected to the closure 6 of the cartridge 3, as will be explained below with reference to the third embodiment.

In the first embodiment, the actuating mechanism 31 is preferably arranged at the lower axial end of the cartridge 3 or the container 4, and/or the actuating mechanism 31 forms a bottom of the cartridge 3 or the container 4.

The actuating mechanism 31 is optionally designed to hold the first plunger 26 and the second plunger 27 in position in the non-actuated state of the actuating mechanism 31 or to secure them against an axial displacement, in particular such that the fluid connection 30 is not unintentionally released.

The first plunger 26 and/or the second plunger 27 can preferably be released by actuating the actuating mechanism 31, preferably in such a way that the first plunger 26 and/or the second plunger 27 are automatically or without further action by a user displaced in the cartridge 3 or the container 4. In this way, a particularly simple and/or user-friendly mixing of the components 2A, 2B is made possible or supported. In particular, all that is necessary to mix the components 2A, 2B is to release the plungers 26, 27 by actuating the actuating mechanism 31.

In the first embodiment, it is provided that a force acts in the direction of the second chamber at least on the second plunger 27, preferably already in the delivery state of the cartridge 3. A negative pressure or vacuum or a pressure which is lower than the ambient pressure preferably prevails in the second chamber 25, preferably such that a tensile force acts on the second plunger 27.

The pressure in the second chamber 25 is preferably less than 100 kPa or 50 kPa, particularly preferably less than 40 kPa or 20 kPa, in particular less than 1000 Pa or 100 Pa and/or more than 100 mPa or 1 Pa, and/or the pressure in the second chamber 25 is at least 10 kPa or 20 kPa, in particular at least 50 kPa or 80 kPa and/or at the most 100 kPa lower than the ambient pressure.

Additionally or alternatively, the force for displacing the plungers 26, 27 can be provided by a spring that is tensioned, in particular already in the delivery state of the cartridge 3. In particular, design solutions are possible in which, in addition or as an alternative to the negative pressure, an elongated spring is arranged in the second chamber 25, which pulls the second plunger 27 in the direction of the closure 6 and/or generates a tensile force in the direction of the closure 6.

The actuating mechanism 31 is designed to withstand the force acting on the second plunger 27 and thus on the container 4.

The actuating mechanism 31 or the actuation element 32 can be actuated by removing the actuating mechanism 31 or the actuation element 32 from the container 4 or the closure 6, by rotating it, by pressing it down and/or by opening or disconnecting the actuating mechanism 31 or the actuation element 32.

In the first embodiment, the actuating mechanism 31 is preferably formed by the actuating element 32, or the actuating mechanism 31 is formed in one piece. However, solutions are also possible in which the actuating mechanism 31 has a plurality of components or is constructed in multiple parts, as will be explained in more detail below.

In the first embodiment, the actuating mechanism 31 or the actuating element 32 can be removed from the bottom of the container 4, in particular pulled off or twisted off, preferably in order to release the first plunger 26 and/or the second plunger 27 and/or to displace it/them axially and/or to transfer the first component 2A from the first chamber 24 via the fluid connection 30 to the second chamber 25 and/or to mix the first component 2A and the second component 2B.

Due to the actuating mechanism 31, it is preferably possible to fluidically connect the chambers 24, 25 to one another or in the unopened state of the cartridge 3 or the container 4, which is sealed off against the outside or against the environment, in particular in a gastight and/or liquid-tight manner, or to mix the components 2A, 2B with each other. In particular, by actuating the actuating mechanism 31, the components 2A, 2B can be brought in contact with each other without opening the cartridge 3 or the chambers 24, 25 to the outside or to the environment. In this way, a particularly sterile or hygienic mixing of the components 2A, 2B is made possible. In particular, liquid is prevented from leaking during the mixing process.

In the first embodiment, actuation of the actuating mechanism 31 or the actuation element 32, in particular a removal of the actuating mechanism 31 or the actuation element 32, preferably does not result in the chambers 24, 25 being opened to the outside or to the environment.

By actuating, in particular removing, the actuating mechanism 31 or the actuating element 32, the first plunger 26 and/or the second plunger 27 is preferably released so that the first plunger 26 and/or the second plunger 27 can, preferably automatically or due to the negative pressure in the second chamber 25, move axially or upward or in the direction of the closure 6, as shown in FIG. 4.

The negative pressure or the tensile force in the second chamber 25 causes, in particular, the second plunger 27 to be displaced together with the first plunger 26 in the direction of the closure 6 or the second chamber 25, in particular such that initially only the volume of the second chamber 25 is reduced.

The first plunger 26 and the second plunger 27 preferably move at least substantially at the same time and/or by the same distance or the same stroke, at least until the second plunger 27 releases the fluid connection 30.

When the second plunger 27 reaches the level of the fluid connection 30 or releases the fluid connection 30, the pressure acting in the second chamber 25 is preferably equalized via the fluid connection 30 and the first chamber 24 or due to the movement of the first plunger 26 or the reduction in size of the first chamber 24.

Due to the negative pressure in the second chamber 25, the first component 2A is preferably sucked from the first chamber 24 via the fluid connection 30 into the second chamber 25 or, after the fluid connection 30 has been released or opened, the volume of the first chamber 24 is reduced or the first plunger 26 is displaced in the direction of the second plunger 27 and/or up to the second plunger 27.

The first plunger 26 is preferably displaced until the first plunger 26 rests at least substantially over its entire surface or with its front side on the second plunger 27, and/or the first component 2A has been at least substantially completely transferred to the second chamber 25, as shown in FIG. 5.

The first plunger 26 and/or the second plunger 27 preferably close the fluid connection 30 when the first plunger 26 rests on the second plunger 27 or assumes its end position.

The negative pressure and/or the friction prevailing between the plungers 26, 27 and the container 4 are/is preferably selected in such a way that the first plunger 26 is in full contact with the second plunger 27, or that the first chamber 24 is completely emptied or the first component 2A is completely transferred to the second chamber 25.

Depending on the selected negative pressure and/or the friction between the plungers 26, 27 and the container 4, the mixing process takes place at different speeds and/or the plungers 26, 27 move, after the components 2A, 2B have been mixed or the first component 2A has been completely transferred to the second chamber 25, together or axially in the direction of the closure 6, as shown in FIG. 5.

The plungers 26, 27 preferably reach their (common) end position when the tensile force acting on the plungers 26, 27, due to the negative pressure, corresponds at least substantially to the frictional force of the plungers 26, 27, with the influence of gravity G being able to be disregarded.

The cartridge 3, in particular the container 4, and particularly preferably the second chamber 25, is filled by at least 80% or 85%, particularly preferably by at least 90% or 95%, with the fluid 2 prepared by mixing the components 2A, 2B in the (joint) end position of the plungers 26, 27 or in the completely mixed state of the components 2A, 2B.

It is particularly preferred if the cartridge 3 or the container 4 or the chambers 26, 27 is/are sealed or closed at both axial ends, in particular at the bottom by the first and/or second plunger 26, 27 and at the top by the closure 6, even after the actuating mechanism 31 has been actuated or during or after the mixing of the components 2A, 2B.

The cartridge 3 prepared in this way can then be inserted into the nebulizer 1 and/or used by means of the nebulizer 1.

Optionally, one of the plungers 26, 27, in particular the first plunger 26, can be removed from or pulled out of the cartridge 3, in particular the container 4, in particular by means of the actuating mechanism 31 or the actuating element 32 and/or after mixing the components 2A, 2B.

In particular, the actuating mechanism 31 or the actuating element 32 can be connected to the first plunger 26, for example, via a connecting part such as a rope or the like.

By removing the first plunger 26, only the second plunger 27 is preferably displaced when a dose of the fluid 2 is removed from the cartridge 3 or the container 4. In this way, the removal of a dose of the fluid 2 is simplified or the friction to be overcome is reduced, as will be explained below with reference to the second embodiment.

It is preferred that the cartridge 3 is open only after the actuating mechanism 31 is actuated or after mixing the components 2A, 2B or after the first component 2A has been transferred from the first chamber 24 to the second chamber 25 to the outside or to the environment or for the removal of a dose of the fluid 2, in particular by means of the conveying element 13, or by inserting the conveying element 13 into the closure 6 and/or by destroying or piercing the seal 7.

The components 2A, 2B are preferably mixed outside the nebulizer 1 or immediately before the cartridge 3 is inserted into the nebulizer 1.

The cartridge 3 especially prepared in this way, i.e., the cartridge 3 with the mixed components 2A, 2B or the fluid 2 in the second chamber 25 that is ready to be dispensed, can then be inserted into the housing 19 and/or opened, for example, in the nebulizer 1, preferably in that the conveying element 13 penetrates the seal 7 and thus opens the cartridge 3 to remove a dose of the fluid 2, as already described in connection with FIG. 1 and FIG. 2.

Alternatively, it can be provided to first insert the cartridge 3 into the nebulizer 1 and only then to mix the components 2A, 2B. In particular, in such a variant of the method, it can be provided that, by inserting the cartridge 3 into the nebulizer 1 or by closing the housing 19, in particular by connecting the lower housing part 21 to the upper housing part 20 or the inner housing part 22, or by tensioning of the nebulizer 1 for the first time, the actuating mechanism 31 or the actuating element 32 is actuated and thus the components 2A, 2B are mixed within the nebulizer 1. For example, by inserting the cartridge 3 into the nebulizer 1 or closing the housing 19 or by tensioning the nebulizer 1 for the first time, the actuating element 32 can be severed, in particular through the lower housing part 21 and in particular in such a way that the plungers 26, 27 are released and the components 2A, 2B are mixed, as already explained.

The nebulizer 1 preferably has an optional air pump 33, in particular in order to put the fluid 2 in the cartridge 3 or in the container 4 under pressure at least temporarily or during the tensioning process, in order to facilitate the removal of the fluid 2 from the cartridge 3 or the container 4 or to support a displacement of the plunger(s) 26, 27 and/or to achieve a pressure equalization in the second chamber 25 after the components 2A, 2B have been mixed, or to balance out a residual negative pressure in the second chamber 25 after components 2A, 2B are mixed for the removal of the fluid 2.

The air pump 33 is preferably arranged in the lower housing part 21 and/or in the bottom of the nebulizer 1, as shown in FIG. 6.

The air pump 33 preferably has a pump plunger 34, a pump cylinder 35 and a pump chamber 36, with the pump plunger 34 preferably being guided axially in the pump cylinder 35 and/or the pump plunger 34 and the pump cylinder 35 delimiting the pump chamber 36. In particular, the air pump 33 is designed to at least temporarily pump air into the cartridge 3 or the container 4.

The air pump 33 preferably works, in particular, exclusively mechanically. In particular, the air pump 33 is preferably activated by the (lifting) movement of the cartridge 3 in the nebulizer 1, in particular by the tensioning of the nebulizer 1.

The air pump 33 preferably allows a predefined or limited pressure increase in the cartridge 3 or in the pump chamber 36.

The pump chamber 36 is at least partially formed in or by the cartridge 3 or by displacing the plungers 26, 27, as shown in FIG. 6.

The air pump 33 preferably has a pump valve 37 with the pump valve 37 being designed to control, in particular to allow and/or prevent, the air supply and the air discharge into the pump chamber 36.

In particular, the pump valve 37 is designed to create a negative pressure in the air pump 33, in particular in the pump chamber 36, during the dispensing process or when a dose of the fluid 2 is dispensed or when the nebulizer 1 is actuated or when the cartridge 3 is moved in the direction of the mouthpiece 17 (not shown in FIG. 6), in particular in that the pump valve 37 opens and/or allows air to be fed into the pump chamber 36.

The pump valve 37 is preferably designed to prevent or limit the discharge of air from the pump chamber 36 during the tensioning process or when the cartridge 3 is moved downwards or when the pump chamber 36 is made smaller, in particular in such a way that the pressure in the pump chamber 36 increases.

FIG. 6 shows a detail of the nebulizer 1 with the inserted cartridge 3 according to the first embodiment, with the nebulizer 1 not being tensioned.

The cartridge 3 or the container 4 preferably forms a part of the air pump 33. In particular, the cartridge 3 or the container 4 forms the pump plunger 34 and/or the cartridge 3, or the container 4 is used as a pump plunger 34 and/or is guided radially in the pump cylinder 35.

In particular, the cartridge 3 or the container 4 acts together with the pump cylinder 35 as a plunger/cylinder arrangement to pump air into the container 4 or into the pump chamber 36 or to increase the pressure in the pump chamber 36 temporarily or during the tensioning process of the nebulizer 1 and thus facilitate the removal of a dose of the fluid 2 from the container 4.

In addition, it is possible to move the plunger(s) 26, 27 by means of the air pump 33 when the nebulizer 1 is operated for the first time in such a way that any negative pressure that may remain in the second chamber 25 after the mixing of the components 2A, 2B is balanced at least substantially completely or is balanced with respect to the environment.

The air pump 33 preferably has a pump ventilation 38, in particular in order to connect the pump valve 37 to the environment (fluidically or pneumatically). The pump ventilation 38 can be formed by an opening, a channel or the like in the housing 19, in particular in the lower housing part 21.

FIG. 7 to FIG. 12 shows the proposed cartridge 3 according to a second embodiment.

The second embodiment of the cartridge 3 corresponds at least substantially to the first embodiment of the cartridge 3.

The statements relating to the first embodiment of the cartridge 3 preferably apply accordingly to the second embodiment of the cartridge 3. In particular, the second embodiment or the cartridge 3 explained in connection with FIG. 7 to FIG. 12 can have one or more features of the first embodiment or the cartridge 3 explained in connection with FIG. 3 to FIG. 6 and/or can be used in general with the nebulizer 1 described in connection with FIG. 1 and FIG. 2.

In contrast to the first embodiment, however, the plungers 26, 27 of the cartridge 3 according to the second embodiment are preferably not or not exclusively automatically displaced in the cartridge 3, for example by a negative pressure in the second chamber 25, but rather (additionally) by a force introduced by means of the actuating mechanism 31 or the actuating element 32. In the second embodiment, a negative pressure or a vacuum can likewise be present in the second chamber 25, or the pressure in the second chamber 25 can, at least in the delivery state of the cartridge 3, be lower than the pressure in the first chamber 24.

Particularly preferably, the actuating mechanism 31 or the actuating element 32 is mechanically connected or coupled to at least the first plunger 26, and/or the actuating mechanism 31 or the actuating element 32 has or forms the first plunger 26, in particular in such a way that when the actuating mechanism 31 or the actuating element 32 are actuated, the first plunger 26 is axially displaced in the cartridge 3 or in the container 4.

The actuating mechanism 31 preferably has a connecting part 39, in particular with the connecting part 39 mechanically connecting/coupling the first plunger 26 and/or the second plunger 27 to the actuating element 32.

The connecting part 39 makes it possible to transmit a movement of the actuating mechanism 31 or the actuating element 32 to the first plunger 26 or the second plunger 27.

In the second embodiment, the actuating mechanism 31 can preferably be actuated by rotating the actuating element 32.

The connecting part 39 is preferably designed to convert the rotary movement of the actuating element 32 into an axial or stroke movement of the first plunger 26 and/or the second plunger 27.

The actuating element 32 is preferably connected to the connecting part 39 in a form-fit, force-fit or cohesive manner, in particular such that a torque can be transmitted from the actuating element 32 to the connecting part 39, or the connecting part 39 is rotated by turning the actuating element 32.

The connecting part 39 is preferably elongated or rod-shaped, in particular as a threaded rod, and/or the connecting part 39 has, at least in part or in portions, a thread, in particular an external thread.

The connecting part 39 preferably extends in particular centrally through the first plunger 26 or the first chamber 24 and/or through the second plunger 27 or into the second chamber 25.

The first plunger 26 and/or the second plunger 27 preferably have/has a corresponding opening or a corresponding bore for the connecting part 39.

In the second embodiment shown, only the first plunger 26 preferably has an opening or a bore, or the connecting part 39 extends only through the first plunger 26 and the first chamber 24 to the second plunger 27.

The second plunger 27 preferably has a receptacle or recess in order to accommodate the axial end of the connecting part 39.

At least the first plunger 26 preferably has an internal thread corresponding to the external thread of the connecting part 39, in particular such that a rotation of the connecting part 39 leads to a displacement of the first plunger 26.

Preferably, the second plunger 27 is, at least in the circumferential direction or in the direction of rotation of the connecting part 39, positively and/or frictionally connected to the connecting part 39, in particular such that a torque can be transmitted from the connecting part 39 to the second plunger 27, or a rotation of the connecting part 39 causes a rotation of the second plunger 27.

The plunger(s) 26, 27 is/are preferably in sealing contact with the connecting part 39, in particular in such a way that the components 2A, 2B are prevented from exiting between the plunger(s) 26, 27 and the connecting part 39.

The connecting part 39 is preferably formed in multiple parts. The connecting part 39 preferably has a first connecting element 39A and a second connecting element 39B, with the first connecting element 39A preferably connecting the second connecting element 39B to the actuating element 32 and/or the second connecting element 39B having or forming an axial end of the connecting part 39.

The connecting part 39 is particularly preferably designed as a telescopic extension or telescopic tube, and/or the connecting part 39 can be extended, in particular telescopically, by rotating the first connecting element 39A relative to the second connecting element 39B.

The connecting elements 39A, 39B are particularly preferably screwed together. The first connecting element 39A preferably has an external thread, and the second connecting element 39B has a corresponding internal thread, with the second connecting element 39B preferably being screwed onto the first connecting element 39A at least in the delivery state of the cartridge 3.

In particular, the second connecting element 39B is designed as a hollow cylinder with an internal thread, and/or the first connecting element 39A is at least partially designed as a threaded rod. However, other solutions are also possible.

The second connecting element 39B preferably has an external profile at least at one end, which allows a torque to be transmitted to the second plunger 27. The second connecting element 39B can, for example, be angular at least at the end.

The first plunger 26 is preferably displaced upwards or in the direction of the closure 6 by turning the actuating mechanism 31 or the actuating element 32 or the connecting part 39. In this way, the distance between the first plunger 26 and the actuating element 32 is increased, or a free space is formed between the actuating element 32 and the second connecting element 39B, which optionally serves as a pump chamber 36 in the nebulizer 1, as already explained on the basis of the first embodiment and for the second embodiment shown in FIG. 12.

In order to prevent a negative pressure from developing in the free space between the actuating element 32 and the first plunger 26 by rotating the actuating element 32, the actuating mechanism 31, in particular the actuating element 32, has an optional ventilation 40, as shown in FIG. 7 to FIG. 10, with the ventilation 40 preferably being designed as a breakthrough, channel, opening or the like in the actuating element 32 and/or fluidically or pneumatically connecting the free space with the environment.

Preferably, however, only the free space between the first plunger 26 and the actuating element 32 is ventilated by the ventilation 40. In particular, the chambers 24 and 25 are still closed or sealed.

Preferably, by actuating the actuating mechanism 31 or the actuating element 32, the in particular telescopic connecting part 39 is extended or lengthened, and/or the second connecting element 39B is axially displaced, in particular together with the first plunger 26.

In particular, due to the rotary movement of the actuating element 32 and thus of the connecting part 39, the second connecting element 39B, which is preferably held by the second plunger 27 in a form-fitting manner, is axially displaced together with the second plunger 27. In this way it is possible to displace both the first plunger 26 and the second plunger 27 in the cartridge 3 by actuating the actuating mechanism 31 or the actuating element 32, in particular at the same time or simultaneously or by the same stroke.

By rotating the actuating element 32, the first chamber 24 is axially displaced together with the first plunger 26 and the second plunger 27, and/or the second chamber 25 is reduced in size, as already explained in connection with the first embodiment.

In particular, the pressure in the second chamber 25 is increased at least temporarily or until the chambers 24, 25 are fluidically connected by actuating the actuating mechanism 31 or the actuating element 32 or by displacing the plungers 26, 27.

Figure 8:
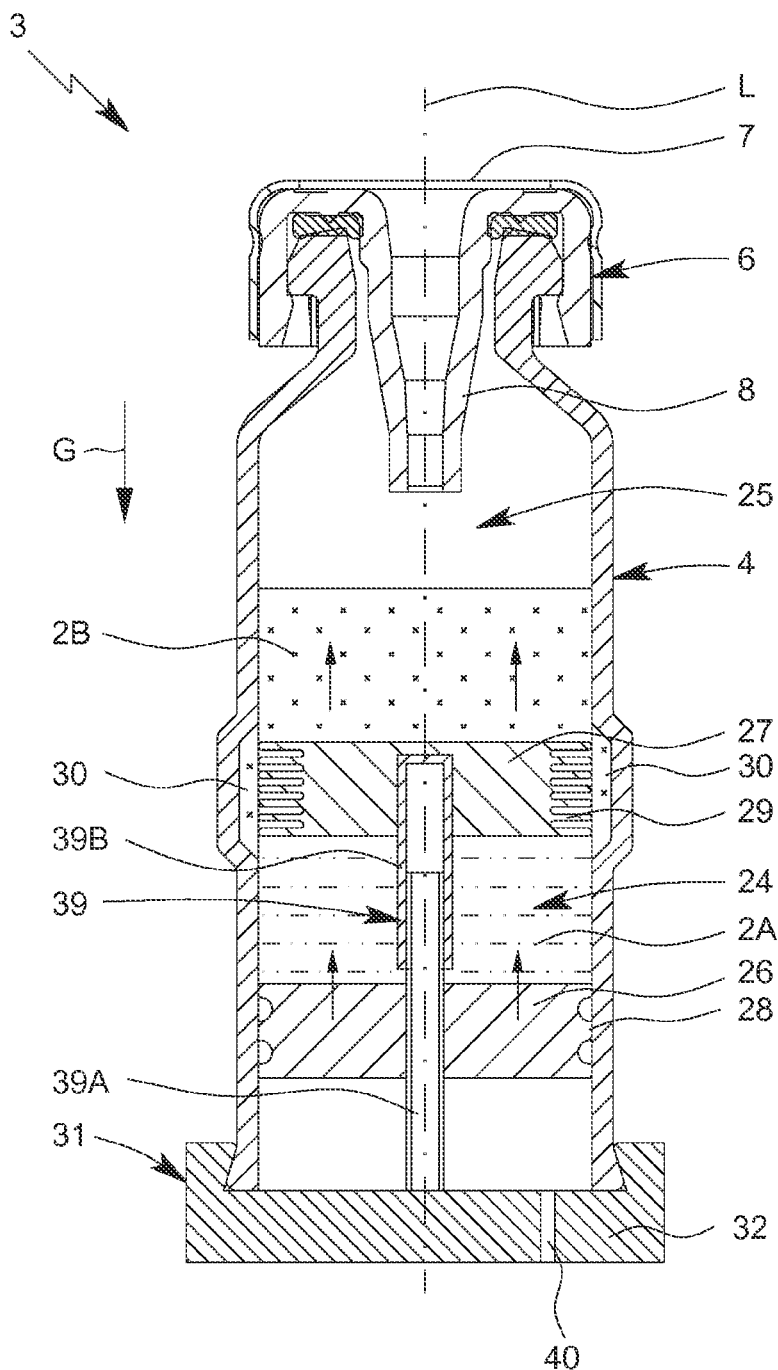

The plungers 26, 27 are preferably displaced by actuating the actuating mechanism 31 or the actuating element 32 in the cartridge 3 or in the container 4 to a position in which the second plunger 27 is arranged at the level of the fluid connection 30, releases the fluid connection 30 and/or the chambers 24, 25 are fluidically connected to one another, as shown in FIG. 8.

By releasing the fluid connection 30, a pressure difference between the chambers 24, 25, in particular brought about by the displacement of the plungers 26, 27, is equalized. In particular, any positive pressure that may have built up in the second chamber 25 is reduced. However, it is also possible that any negative pressure that may be present in the second chamber 25 is equalized by fluidically connecting the chambers 24, 25.

In the second embodiment shown, a plurality of fluid connections 30, here two fluid connections 30, are preferably provided, in particular in order to facilitate an outflow of the first component 2A from the first chamber 24.

As soon as the plungers 26, 27 have reached the position for mixing the components 2A, 2B, the mixing process can be carried out.

The nebulizer 1 preferably indicates to a user, in particular optically, acoustically and/or haptically, when the actuation or rotation of the actuation element 32 is to be set for the mixing of the components 2A, 2B or when the mixing process can be started or when the position is reached in which the fluid connection 30 is released. The cartridge 3 or the container 4, for example, can be transparent at least partially or in portions and/or have a viewing window in order to be able to see the first plunger 26 and/or the second plunger 27 from the outside, especially when the plunger(s) 26, 27 has/have reached the position for mixing the components 2A, 2B.

Figure 9:
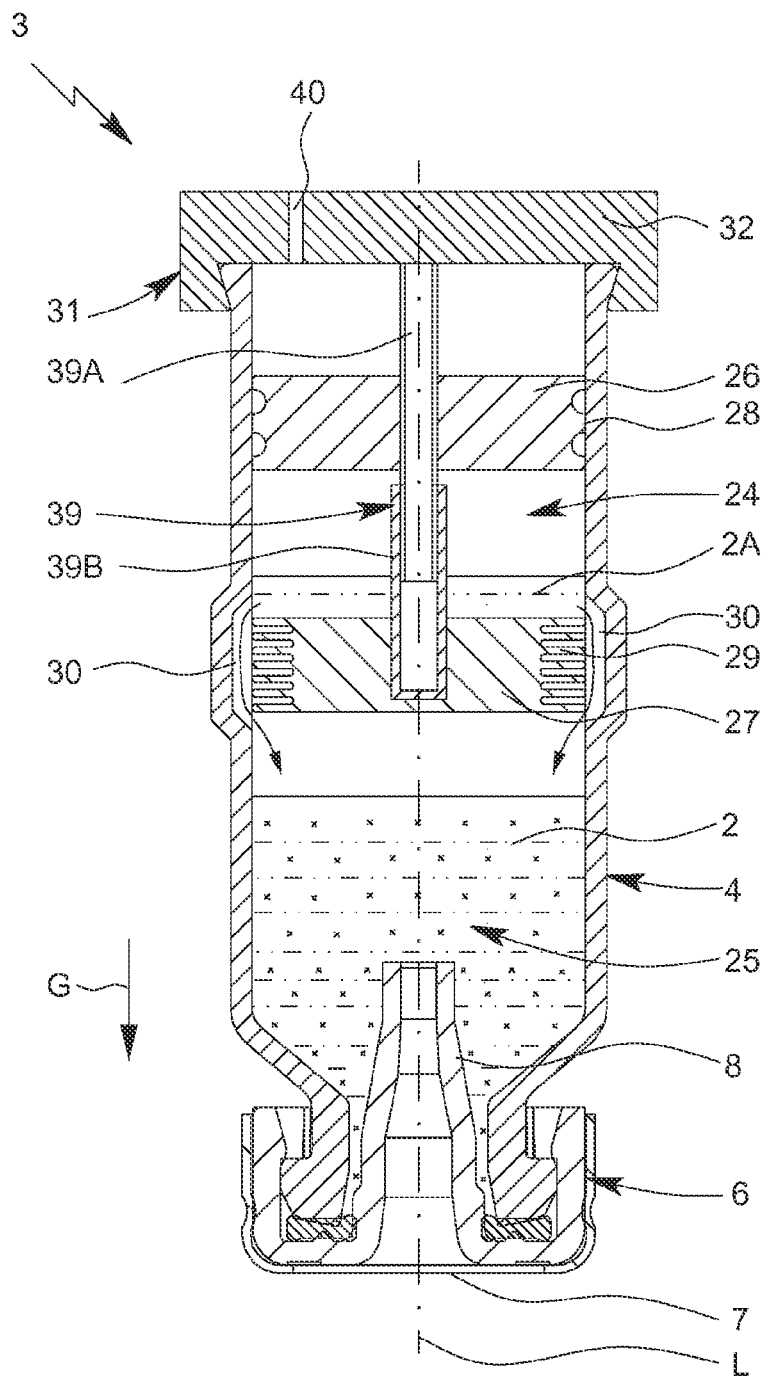

The mixing process is preferably initiated after the fluid connection(s) 30 has/have been released. For this purpose, the cartridge 3 is aligned such that the first chamber 24 is arranged above the second chamber 25, and/or the force of gravity G transfers the first component 2A from the first chamber 24 via the fluid connection(s) 30 to the second chamber 25, as shown in FIG. 9.

The fluid connection(s) 30 is or are in particular dimensioned such that the first component 2A flows from the first chamber 24 into the second chamber 25 exclusively as a result of the force of gravity G and/or without an (additional) force, and/or an in particular simultaneous venting of the second chamber 25 or an in particular simultaneous outflow of a gas from the second chamber 25 into the first chamber 24 takes place.

As already mentioned, in the second embodiment, no negative pressure or vacuum is preferably required in the second chamber 25. A gas that is present in the second chamber 25 for technical production considerations, for example, can flow/escape from the second chamber 25 into the first chamber 24 or upwards when the components 2A, 2B are mixed via the fluid connection(s) 30. Consequently, the second chamber 25 is filled at the same time as the second chamber 25 is vented.

However, it is also possible that a negative pressure or vacuum is provided likewise in the second chamber 25 of the second embodiment, for example in order to support the displacement of the plungers 26, 27.

Figure 10:
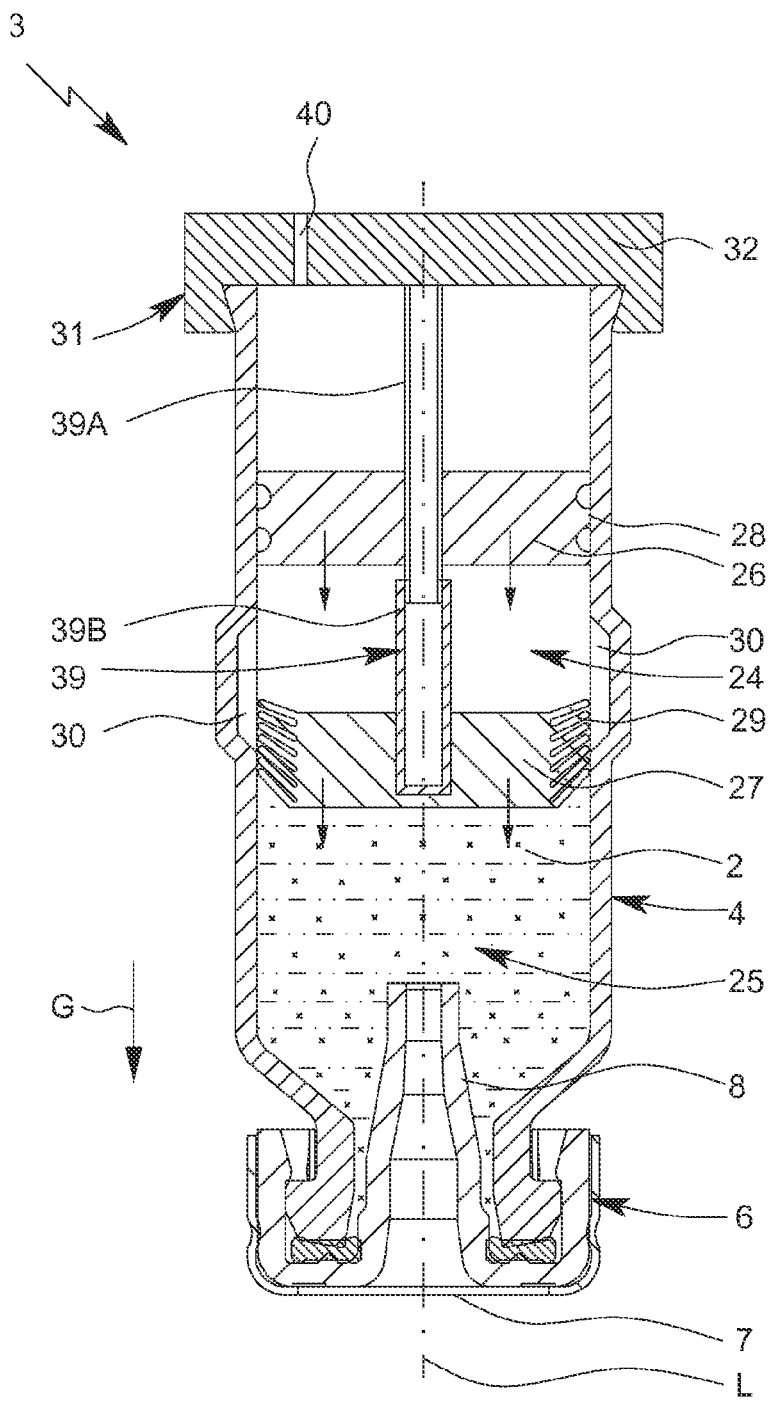
Figure 11:
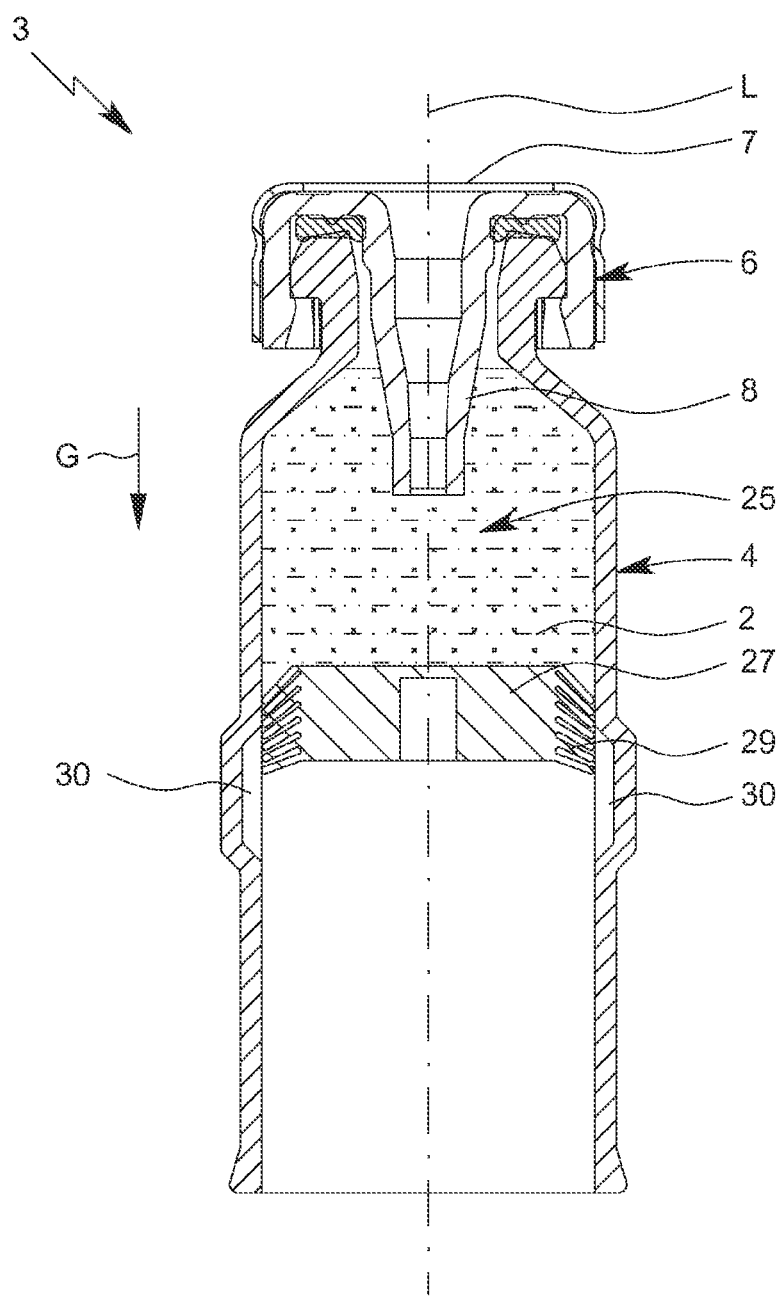

As soon as the first chamber 24 is completely emptied, or the mixing process is completed, the actuating mechanism 31 or the actuating element 32 is preferably actuated once more, in particular rotated, in particular in order to close the fluid connection(s) 30 again, in particular by means of the second plunger 27, as shown in FIG. 10.

In particular, by actuating the actuating mechanism 31 or the actuating element 32 once more, the connecting part 39 is further extended or deployed, and/or the second connecting element 39B or the second plunger 27 is further displaced in the axial direction, in particular beyond the fluid connection(s) 30 or in the direction of the closure 6, particularly preferably until the second plunger 27 (again) rests fully or radially on the wall of the cartridge 3 or the container 4 and/or closes the fluid connection(s) 30.

After the fluid connection(s) 30 have been closed and/or due to the (subsequent) displacement of the plungers 26, 27, the pressure in the second chamber 25 is preferably (again) increased or a pressure difference is built up between the chambers 24, 25, in particular such that the pressure in the second chamber 25 is greater than the pressure in the first chamber 24.

The plunger seal 29 of the second plunger 27 is preferably designed to be flexible or resilient and/or lamella-like. In particular, when a predetermined pressure in the second chamber 25 is exceeded, the plunger seal 29 of the second plunger 27 can yield or partially open in such a way that a gas or a liquid penetrates at least partially into the plunger seal 29, as indicated in FIG. 10. This makes it possible to push a gas enclosed in the second chamber 25 into the plunger seal 29 by moving the second plunger 27 in the direction of the closure 6, in particular such that the second chamber 25 is at least substantially gas-free, and/or the volume of the enclosed gas in the second chamber 25 is minimized.

The release of the fluid connection(s) 30 or the mixing of the components 2A, 2B takes place particularly preferably in the unopened or gastight or fluid-tight state of the cartridge 3. In particular, the cartridge 3, the container 4 and the chambers 24, 25 are also sealed or closed during or after the release or mixing, in particular at the bottom by the first and/or second plunger 26, 27 and at the top by the closure 6.

Particularly preferably, the same or corresponding comments and explanations apply to the opening of the cartridge 3 as those provided with regard to the first embodiment. In particular, the opening takes place only after the components 2A, 2B have been mixed. The opening can take place before, after or by the insertion into the nebulizer 1.

As already explained, the actuating mechanism 31 can preferably—in particular completely—be removed from the cartridge 3, in particular from the container 4 and/or closure 6, in particular in order to be able to insert the cartridge 3 into the nebulizer 1 after the components 2A, 2B have been mixed.

FIG. 11 shows the cartridge 3 with the actuating mechanism 31 removed and thus in the state ready for use.

The actuating mechanism 31, in particular the actuating element 32 and/or the connecting part 39, is preferably removable together with the first plunger 26 or can be pulled out of the cartridge 3 or the container 4.

By removing the actuating element 32, the first plunger 26 is preferably removed from the cartridge 3 or pulled out of the container 4. Solutions are also possible, however, in which both the first plunger 26 and the second plunger 27 remain in the cartridge 3 or in the container 4, as explained in connection with the first embodiment.

The optional removal of the first plunger 26 from the cartridge 3 or the container 4 has the advantage that only the second plunger 27 has to be displaced to remove a dose of the fluid 2, resulting in less friction in the cartridge 3. In this way, the removal of a dose of the fluid 2 is facilitated.

As already explained in connection with the first embodiment, the withdrawal of a dose of the fluid 2 or the movement of the second plunger 27 can be supported by an optional air pump 33, as shown in FIG. 12.

FIG. 12 shows the nebulizer 1 with an inserted cartridge 3 according to the second embodiment, wherein, in contrast to the nebulizer 1 shown in FIG. 6, the nebulizer 1 is shown in the tensioned state. The statements made in connection with FIG. 6 apply accordingly.

Optionally, the cartridge 3, in particular the container 4, has a-preferably integrated-mixing device such as a stirrer (not shown), preferably wherein the mixing device is designed to support the mixing of the components 2A, 2B.

The cartridge 3, in particular the container 4, can, for example, have a stirrer, particularly preferably a screw stirrer, a propeller stirrer, an inclined blade stirrer, a grid stirrer, a blade stirrer or the like, preferably with the stirrer being fixedly connected to the second plunger 27, in particular in a form-fit, force-fit and/or cohesive manner, and in particular such that a rotary movement transferred to the second plunger 27 by the actuating element 32 is transferred to the stirrer.

The mixing of the components 2A, 2B in the second chamber 25 is supported by the optional mixing device.

Additionally or alternatively, the second plunger 27 can have or form a mixing device. The side of the second plunger 27 facing the second chamber 25 can, for example, be roughened and/or has elevations or depressions, preferably in order to generate eddies or turbulences in the fluid 2 and thus support the mixing process.

FIG. 13 to FIG. 16 show the cartridge 3 according to a third embodiment.

The statements relating to the first and/or second embodiment of the cartridge 3 preferably apply accordingly to the third embodiment of the cartridge 3. In particular, the third embodiment or the cartridge 3 explained in connection with FIG. 13 to FIG. 16 can have one or more features of the first and/or second embodiment or the cartridge 3 explained in connection with FIG. 3 to FIG. 6 or FIG. 7 to FIG. 12 and/or can basically be used in connection with the nebulizer 1 described in FIG. 1 and FIG. 2.

In the third embodiment, the actuating mechanism 31 is preferably arranged on the closure 6 of the cartridge 3 and/or connected to the closure 6 of the cartridge 3, in particular in a form-fit, force fit and/or cohesive manner.

In particular, the actuating mechanism 31 forms a top part, a cap or the like for the cartridge 3 or the closure 6. Design solutions are also possible in which the actuating mechanism 31 is integrated into the closure 6 of the cartridge 3.

The actuating mechanism 31 preferably has a base body 41, with the base body 41 preferably being connected to the closure 6 in a form-fit, force-fit and/or cohesive manner.

In the third embodiment shown, the actuating mechanism 31, in particular the base body 41, is preferably plugged onto the closure 6, in particular in a releasable manner and in such a way that the actuating mechanism 31 can be removed from the closure 6.

The first chamber 24 is preferably integrated into the actuating mechanism 31, or the actuating mechanism 31 contains the first chamber 24 or the first component 2A of the fluid 2.

In particular, the actuating mechanism 31, preferably the base body 41, forms a reservoir or the first chamber 24 for the first component 2A.

The actuating mechanism 31 preferably comprises the first plunger 26, and/or the first plunger 26 is embedded into the actuating mechanism 31 or the base body 41.

In particular, the first plunger 26 closes the first chamber 24 in the axially upward direction, and/or the base body 41 delimits the first chamber 24 laterally or radially and/or in the axially downward direction.

The first chamber 24 is preferably at least substantially cylindrical. Other solutions are also possible here, however, in particular solutions in which the first chamber 24 is annular and/or extends annularly around the longitudinal axis L or—in particular in a plan view of the cartridge 3—around the closure 6. The actuating mechanism 31, in particular the base body 41, particularly preferably has a central recess or a central opening through which the conveying element 13 of the nebulizer 1 can be introduced into the closure 6 or the connection 8, in particular without removing the actuating mechanism 31 beforehand.

The actuating element 32 preferably forms the plunger 26, and/or the actuating element 32 is integrally formed with the plunger 26.

In particular, by actuating the actuating mechanism 31 or the actuating element 32, the chamber 24 in the base body 41 can be reduced, in particular such that the component 2A contained in the chamber 24 reaches the second chamber 25 via the fluid connection 30, as will be explained below.

The actuating mechanism 31, in particular the base body 41, preferably extends or projects into the container 4 and/or the closure 6.

The actuating mechanism 31, in particular the base body 41, preferably has an in particular elongated connecting piece 42, preferably with the connecting piece 42 protruding at least partially into the container 4 or the second chamber 25.

In the embodiment shown, the base body 41 and the connecting piece 42 are formed in one piece. However, other solutions are also possible in this regard.

The connecting piece 42 is preferably designed to fluidically connect the first chamber 24 to the second chamber 25.

Preferably, the actuating mechanism 31, particularly preferably the base body 41, in particular the connecting piece 42, has or forms the fluid connection 30.

In the embodiment shown, the connecting piece 42 is at least substantially cylindrical or designed as a cylindrical hollow body and/or is funnel-shaped. Other solutions are also possible, however, in particular solutions in which the connecting piece 42 extends ring-like around the longitudinal axis L or the closure 6.

The closure 6 preferably has an opening 45 through which the connecting piece 42 extends or into which the actuating mechanism 31, particularly preferably the base body 41, in particular the connecting piece 42, is inserted.

The first chamber 24, in particular the connecting piece 42, is preferably closed or sealed—at least in the delivery state of the cartridge 3—in particular in such a way that the first component 2A is prevented from exiting from the first chamber 24 into the second chamber 25.

The actuating mechanism 31 particularly preferably has a closure element 43, with the closure element 43 preferably closing the first chamber 24 or the connecting piece 42 at the bottom or opposite the second chamber 25. The closure element 43 is preferably designed as a seal, film, stopper or the like and/or attached to the axial or free end of the connecting piece 42.

The actuating mechanism 31, in particular the first chamber 24, can preferably be opened by actuating the actuating mechanism 31 or the actuating element 32 or the plunger 26.

Figure 14:
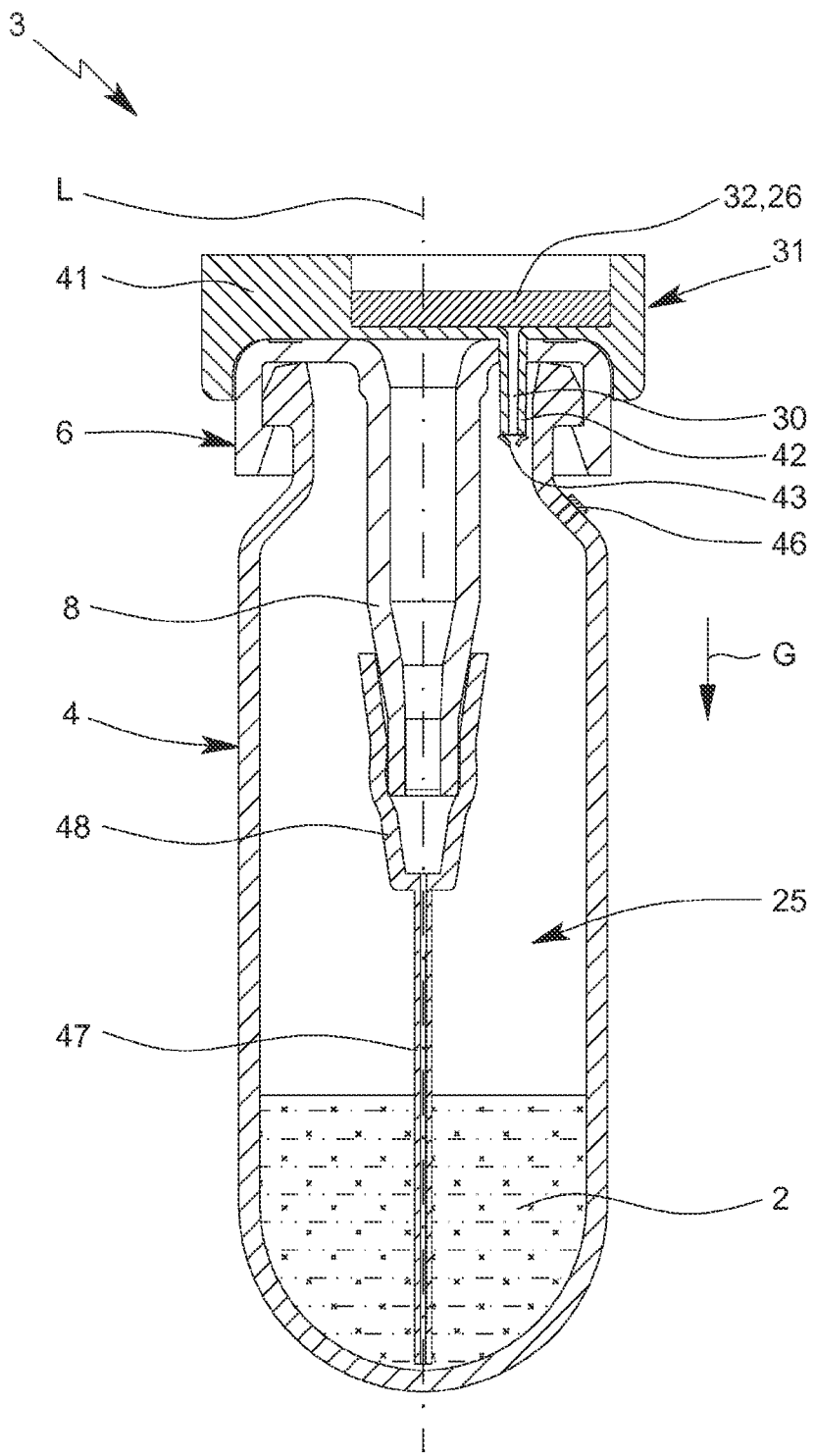

The closure element 43 is preferably at least partially opened, folded away and/or destroyed or separated when the actuating mechanism 31 or the actuating element 32 or the plunger 26 is actuated, as shown schematically in FIG. 14.

Optionally, the actuating mechanism 31, in particular on a side facing away from the container 4, has a cover 44 such as a film or the like, with the cover 44 preferably being designed to prevent an accidental actuation of the actuating mechanism 31 and/or leakage from the chamber 24. Preferably, the cover 44 for actuating the actuating mechanism 31 can be removed, in particular pulled off, from the base body 41, as indicated in FIG. 13.

To mix the components 2A, 2B in the cartridge 3, the cover 44 is removed or pulled off from the actuating mechanism 31 or the base body 41 in a first optional step.

The chambers 24, 25 are preferably sealed or closed even after the cover 44 has been removed or pulled off, in particular at the bottom by the container 4 and at the top by the plunger 26.

The actuating mechanism 31 or the actuating element 32 is then actuated or pushed down, in particular such that the first component 2A is pushed or transferred from the actuating mechanism 31, in particular the first chamber 24, into the container 4 or the second chamber 25.

In particular, by actuating the actuating mechanism 31 or by pushing the actuating element 32 or the plunger 26 down, the pressure in the first chamber 24 is increased until the closure element 43 releases the connecting piece 42 or the fluid connection 30, and/or a fluid connection is established between the first chamber 24 and the second chamber 25 or between the actuating mechanism 31 and the container 4.

Subsequently, the volume of the first chamber 24 can be reduced by pushing down the actuating element 32, and thus the first component 2A can be guided from the first chamber 24 to the second chamber 25 via the connecting piece 42 or the fluid connection 30.

FIG. 14 shows the cartridge 3 with the actuating mechanism 31 or the chamber 24 already completely emptied.

The cartridge 3, the container 4 and the chambers 24, 25 are also sealed or closed whilst or after the actuating mechanism 31 is actuated or the actuation element 32 or the plunger 26 is pushed down.

The same or similar comments and explanations apply, particularly preferably to the opening of the cartridge 3, as those made with regard to the first embodiment. In particular, the opening takes place only after the components 2A, 2B have been mixed. The opening can take place before, after or by the insertion into the nebulizer 1.

It is preferred that the actuating mechanism 31 is to be removed or pulled off from the cartridge 3, in particular the closure 6, after the components 2A, 2B have been mixed, in particular before the cartridge 3 is inserted into the nebulizer 1. FIG. 15 shows a corresponding illustration of the cartridge 3 with the actuating mechanism 31 removed so that the illustrated cartridge 3 can be inserted into the nebulizer 1.

Solutions are also possible, however, in which the actuating mechanism 31 is integrated into the closure 6 and/or forms the closure 6. As already explained, the actuating mechanism 31 can, for example, have a corresponding central recess or bore so that the conveying element 13 is inserted into the connection 8 by the actuating mechanism 31 or so that the conveying element 13 extends, in the inserted state of the cartridge 3, through the actuating mechanism 31 into the container 4 or the second chamber 25. In this case, it is preferred to insert the cartridge 3 together with the actuating mechanism 31 into the nebulizer 1.

The cartridge 3 is preferably opened to the surroundings or the outside by removing the actuating mechanism 31 from the cartridge 3 or the closure 6, in particular by pulling the connecting piece 42 out of the opening 45. In the inserted state of the cartridge 3, the opening 45 can serve as a vent for the container 4. Alternatively, the opening 45 can be closed, for example, by a plug and/or the holder 11 of the nebulizer 1.

In the third embodiment, the opening can likewise take place before, after or by the insertion into the nebulizer 1. If the actuating mechanism 31 is removable for inserting the cartridge 3, the cartridge 3 is preferably opened as a result of this or before it is inserted into the nebulizer 1, as explained above. In solutions in which the actuating mechanism 31 is inserted into the nebulizer 1 together with the cartridge 3, an opening during or after the insertion is possible as well.

Furthermore, the same or corresponding comments and explanations as in the first and/or second embodiment preferably apply to the opening of the cartridge 3. In particular, the opening takes place only after the components 2A, 2B have been mixed.

The cartridge 3 preferably has an optional ventilation valve 46, with the ventilation valve 46 preferably being arranged in the wall of the container 4 and/or allowing a fluidic or pneumatic connection of the cartridge 3 to the outside or the environment.

A pressure equalization to the outside or between the container 4 or the second chamber 25 and the environment is preferably made possible by the opening 45 and/or the ventilation valve 46.

In the third embodiment shown, the volume of the second chamber 25 or the container 4 preferably does not decrease during the removal of a dose of the fluid 2. By tensioning the nebulizer 1 or by withdrawing a dose of the fluid 2, a negative pressure thus preferably arises in the second chamber 25 or in the container 4, which is equalized in particular by the opening 45 and/or the ventilation valve 46.

In addition, by means of the ventilation valve 46, it is possible to avoid positive pressure in the container 4 when the actuating mechanism 31 is actuated or when the first component 2A is pressed into the second chamber 25 or into the container 4.

The illustrated cartridge 3 preferably has an in particular flexible conveying tube 47 and/or an adapter 48, with the conveying tube 47 preferably being fluidically connected to the closure 6 or the connection 8, in particular via the adapter 48.

The conveying tube 47 preferably serves as an extension of the conveying element 13 and/or allows the fluid 2 to be removed at least substantially independently of the orientation of the nebulizer 1 or the cartridge 3.

The conveying tube 47 is optionally designed as a stirrer, and/or the conveying tube 47 serves to support mixing of the components 2A, 2B in the cartridge 3 or the container 4. Design solutions are possible, for example, in which the conveying tube 47 is formed in a spiral.

Design solutions are also possible, however, in which the cartridge 3 or the container 4 has the flexible bag 5 that was explained in connection with FIG. 1 and FIG. 2, with the bag 5 preferably comprising or forming the second chamber 25.

Alternatively, the cartridge 3 can also have a second plunger 27 in the third embodiment, with the second plunger 27 preferably closing the container 4 or the second chamber 25 at the bottom, as already explained in connection with the first and second embodiment. In the case of alternative designs of this type, the conveying tube 47, adapter 48 and/or ventilation valve 46 shown can be dispensed with.

FIG. 16 shows the nebulizer 1 with an inserted cartridge 3 according to the third embodiment.

ALTERNATIVE COMBINATIONS

Further aspects of the present invention that can also be realized independently are listed below:

1. Cartridge (3) for a nebulizer (1) for nebulizing a fluid (2),
   wherein the fluid (2) is a medicament composed of or produced from at least two components (2A, 2B),
   wherein the cartridge (3) comprises a container (4) and a closure (6) for the fluidic and/or sealing connection of the container (4) to the nebulizer (1),
   wherein the cartridge (3) comprises at least two fluidically separated chambers (24, 25) with the chambers (24, 25) each containing at least one of the components (2A, 2B) of the fluid (2),
   characterized in that a first chamber (24) contains a solution, in particular an ethanolic lipid solution, as the first component (2A) of the medicament, and a second chamber (25) contains an aqueous buffer as the second component (2B) in order to produce a liposomal medicament by combining the components (2A, 2B).
2. Cartridge according to aspect 1, characterized in that the chambers (24, 25) can be fluidically connected to one another by actuating an actuating mechanism (31) in order to mix the components (2A, 2B) for producing the fluid (2).
3. Cartridge according to aspect 2, characterized in that the chambers (24, 25) in the unopened state of the cartridge (3) or the container (4) in the stage when it is sealed from the outside or from the environment, in particular in a gastight and/or liquid-tight manner, can be fluidically connected to one another by actuating the actuating mechanism (31).
4. Cartridge according to either aspect 2 or aspect 3, characterized in that at least one of the chambers (24, 25), preferably all of the chambers (24, 25), can be reduced in size by actuating the actuating mechanism (31), and/or the component (2A, 2B) is at least partially transferable from one of the chambers (24, 25) to another of the chambers (24, 25).
5. Cartridge according to any of aspects 1 to 4, characterized in that one component (2A, 2B) is a liquid, in particular a solvent or suspension medium, and/or another component (2A, 2B) is a medicinal agent, in particular a solid, lyophilized, encapsulated and/or powdered medicinal agent.
6. Cartridge system with a cartridge (3), preferably according to any of aspects 1 to 5, and an actuating mechanism (31),
   wherein the cartridge (3) comprises a container (4) and a closure (6) for the fluidic and/or sealing connection of the container (4) to a dispensing device, in particular a nebulizer (1),
   wherein the cartridge (3) comprises at least two fluidically separated chambers (24, 25) with the chambers (24, 25) each containing a component (2A, 2B) of a fluid (2) to be produced from at least two components (2A, 2B),
   wherein the chambers (24, 25) can be fluidically connected to one another by actuating the actuating mechanism (31) in order to mix the components (2A, 2B) for producing the fluid (2).
7. Cartridge system according to aspect 6, characterized in that the actuating mechanism (31), in particular after actuating the actuating mechanism (31), can be removed, preferably by twisting or pulling it off the container (4) and/or the closure (6).
8. Cartridge system according to either aspect 6 or aspect 7, characterized in that the actuating mechanism (31) axially closes the cartridge (3), in particular the container (4) and/or the closure (6), and/or comprises an axial end, in particular a base and/or a lid which has or forms a cartridge (3) and/or is integrated into the container (4) or closure (6).
9. Cartridge system according to any of aspects 6 to 8, characterized in that the actuating mechanism (31) comprises an actuating element (32), with the actuating mechanism (31) being able to be actuated by removing the actuating element (32) from the container (4) or closure (6) by rotating, by pushing down and/or by opening or separating the actuating element (32).
10. Cartridge system according to any of aspects 6 to 9, characterized in that the actuating mechanism (31) and/or the container (4) comprises or forms at least one fluid connection (30), in particular a bypass, wherein preferably, by actuating the actuating mechanism (31), the fluid connection (30) can be released or opened and/or the chambers (24, 25) can be fluidically connected to one another via the fluid connection (30).

11. Cartridge system according to any of aspects 6 to 10, characterized in that the cartridge (3), in particular the container (4) and/or the actuating mechanism (31), comprises at least one or two movable plungers (26, 27), wherein preferably the plunger(s) (26, 27) can be displaced by actuating the actuating mechanism (31) in the cartridge (3) or in the container (4) or in the actuating mechanism (31), and/or (each) forms a wall of the chambers (24, 25).

12. Cartridge system according to aspect 11, characterized in that the plunger(s) (26, 27) in the cartridge (3) or in the container (4) can be released by actuating the actuating mechanism (31), in particular such that the plunger(s) (26, 27) displace(s) automatically in the cartridge (3) or in the container (4), preferably by a force acting in the direction of one of the chambers (24, 25), particularly preferably by a tensile force generated in particular by negative pressure in one of the chambers (24, 25).

13. Cartridge system according to aspect 11, characterized in that the actuating mechanism (31), in particular the actuating element (32), is mechanically coupled to the plunger(s) (26, 27)—in particular by means of a connecting part (39)—and/or in that, by rotating the actuating mechanism (31), in particular the actuating element (32), the plunger(s) (26, 27) can be displaced in the cartridge (3) or at least one of the chambers (24, 25), preferably all of the chambers (24, 25), can be reduced in size.

14. Nebulizer (1) for nebulizing a fluid (2) which is a medicament composed of or produced from at least two components (2A, 2B), wherein the nebulizer (1) comprises a preferably replaceable cartridge (3), a housing (19) for accommodating the cartridge (3) and a pump (9), wherein the pump (9) is designed to remove a dose of the fluid (2) from the cartridge (3) and to apply pressure to the corresponding dose for nebulizing the fluid (2), characterized in that the cartridge (3) is designed according to any of aspects 1 to 5, or the cartridge (3) corresponds to the cartridge (3) from the cartridge system according to any of aspects 6 to 13, in particular after removing the actuating mechanism (31).

15. Method for preparing a fluid (2) in a cartridge (3) for nebulization by means of a nebulizer (1), with the cartridge (3) preferably being designed according to any of aspects 1 to 5 and/or the nebulizer (1) being designed according to aspect 14, wherein the fluid (2) is a medicament composed of or produced from at least two components (2A, 2B), wherein a plurality of chambers (24, 25) of the cartridge (3) which are initially fluidically separated from one another are fluidically connected to one another, wherein a component (2A, 2B) of the fluid (2) is at least partially transferred from one of the chambers (24, 25) to another of the chambers (24, 25) with a further component (2A, 2B) of the fluid (2) in order to mix the components (2A, 2B), characterized in that the cartridge (3) is only opened to remove a dose of the fluid (2) after the components (2A, 2B) have been mixed.

16. Method according to aspect 15, characterized in that the mixing of the components (2A, 2B) takes place outside the nebulizer (1) or independently of the nebulizer (1), and/or in that the cartridge (3) is inserted into the nebulizer (1) and/or fluidically connected to the nebulizer (1) only after the mixing of the components (2A, 2B) and/or after the opening of the cartridge (3), and/or in that the cartridge (3) in the nebulizer (1) is opened, and/or in that the chambers (24, 25) are fluidically connected to one another after or by inserting the cartridge (3) into the nebulizer (1), in particular by closing a housing (19) of the nebulizer (1).
17. Method according to either aspect 15 or aspect 16, characterized in that one of the components (2A, 2B) is automatically transferred from one chamber to the other chamber (24, 25) by actuating an actuating mechanism (31), in particular by a force generated by negative pressure in one of the chambers (24, 25), and/or in that the cartridge (3) is, after the chambers (24, 25) have been connected or after a fluid connection (30) between the chambers (24, 25) has been released, aligned such that a component (2A, 2B) is transferred from one chamber to the other chamber (24, 25)—in particular exclusively—by gravity (G), and/or in that an actuating mechanism (31) for connecting the chambers (24, 25) is removed from the cartridge (3) after actuating the actuating mechanism (31), in particular to insert the cartridge (3) into the nebulizer (1).
18. Nebulizer (1) for nebulizing a fluid (2), wherein the fluid (2) is a medicament composed of or produced from at least two components (2A, 2B), wherein the nebulizer (1) comprises a preferably replaceable cartridge (3), a housing (19) for accommodating the cartridge (3) and a pump (9), wherein the pump (9) is designed to remove a dose of the fluid (2) from the cartridge (3) and to apply pressure to the corresponding dose for nebulizing the fluid (2), characterized in that the cartridge (3) is designed according to any of aspects 19 to 30.

19. Cartridge (3) for a nebulizer (1) for nebulizing a fluid (2), wherein the fluid (2) is a medicament composed of or produced from at least two components (2A, 2B), wherein the cartridge (3) comprises a container (4) and a closure (6) for the fluidic and/or sealing connection of the container (4) to the nebulizer (1), wherein the cartridge (3) comprises at least two fluidically separated chambers (24, 25) with the chambers (24, 25) each containing at least one of the components (2A, 2B) of the fluid (2), characterized in that the cartridge (3) comprises an in particular removable actuating mechanism (31), with the chambers (24, 25) being fluidically connectable to one another by actuating the actuating mechanism (31) in order to mix the components (2A, 2B) so as to provide or produce or nebulize the fluid (2) and/or to generate the fluid (2), in particular a liposomal medicament, by combining or mixing the components (2A, 2B), and/or in that a first chamber (24) contains a solution, in particular an ethanolic lipid solution, as the first component (2A) of the medicament, and a second chamber (25) contains an aqueous buffer as the second component (2B) in order to produce a liposomal medicament by combining the components (2A, 2B).

20. Cartridge according to aspect 19, characterized in that the chambers (24, 25) in the unopened state of the cartridge (3) or the container (4) or in the stage when it is sealed from the outside or from the environment, in particular in a gastight and/or liquid-tight manner, can be fluidically connected to one another by actuating the actuating mechanism (31).
21. Cartridge according to either aspect 19 or aspect 20, characterized in that at least one of the chambers (24, 25), preferably all of the chambers (24, 25), can be reduced in size by actuating the actuating mechanism (31), and/or the component (2A, 2B) is at least partially transferable from one of the chambers (24, 25) to another of the chambers (24, 25).
22. Cartridge system according to any of aspects 19 to 21, characterized in that the actuating mechanism (31) axially closes the cartridge (3), in particular the container (4) and/or the closure (6), and/or comprises an axial end, in particular a base and/or a lid which has or forms a cartridge (3) and/or is integrated into the container (4) or closure (6).
23. Cartridge according to any of aspects 19 to 22, characterized in that the actuating mechanism (31) comprises an actuating element (32) with the actuating mechanism (31) being able to be actuated by removing the actuating element (32) from the container (4) or closure (6) by rotating, by pushing down and/or by opening or separating the actuating element (32).
24. Cartridge according to any of aspects 19 to 23, characterized in that the actuating mechanism (31)—in particular after actuating the actuating mechanism (31)—can be removed from the container (4) and/or closure (6), in particular twisted off or pulled off, preferably to open the cartridge (3) outward and/or to insert said cartridge into the nebulizer (1).
25. Cartridge according to any of aspects 19 to 24, characterized in that the actuating mechanism (31) and/or the container (4) comprises or forms at least one fluid connection (30), in particular a bypass, wherein preferably by actuating the actuating mechanism (31), the fluid connection (30) can be released or opened and/or the chambers (24, 25) can be fluidically connected to one another via the fluid connection (30).
26. Cartridge according to any of aspects 19 to 25, characterized in that the cartridge (3), in particular the container (4) and/or the actuating mechanism (31), has at least one or two movable plungers (26, 27) with the plunger(s) (26, 27) preferably being able to be displaced by actuating the actuating mechanism (31) in the cartridge (3) or in the container (4) or in the actuating mechanism (31), and/or with (each) forming a wall of the chambers (24, 25).
27. Cartridge according to aspect 26, characterized in that the plunger(s) (26, 27) in the cartridge (3) or in the container (4) can be released by actuating the actuating mechanism (31), in particular such that the plunger(s) (26, 27) displace(s) automatically in the cartridge (3) or in the container (4), preferably by a force acting in the direction of one of the chambers (24, 25), particularly preferably by a tensile force, generated in particular by negative pressure in one of the chambers (24, 25).
28. Cartridge according to aspect 26, characterized in that the actuating mechanism (31), in particular the actuating element (32), is mechanically coupled to the plunger(s) (26, 27)—in particular by means of a connecting part (39)—and/or in that, by rotating the actuating mechanism (31), in particular the actuating element (32), the plunger(s) (26, 27) can be displaced in the cartridge (3), or at least one of the chambers (24, 25), preferably all of the chambers (24, 25), can be reduced in size.
29. Cartridge according to any of aspects 19 to 28, characterized in that one component (2A, 2B) is a liquid, in particular a solvent or suspension medium, and/or another component (2A, 2B) is a medicinal agent, in particular a solid, lyophilized, encapsulated and/or powdered medicinal agent.
30. Cartridge according to any of aspects 19 to 29, characterized in that the cartridge (3), in particular the container (4) and/or the second plunger (27), has or forms a mixing device, in particular a stirrer, in particular to support a mixing of the components (2A, 2B).
31. Method for preparing a fluid (2) in a cartridge (3) for nebulization by means of a nebulizer (1) with the cartridge (3) preferably being designed according to any of aspects 19 to 30 and/or the nebulizer (1) being designed according to aspect 18,
wherein the fluid (2) is a medicament composed of at least two components (2A, 2B),
wherein a plurality of chambers (24, 25) of the cartridge (3) which are initially fluidically separated from one another are fluidically connected to one another,
wherein a component (2A, 2B) of the fluid (2) is at least partially transferred from one of the chambers (24, 25) to another of the chambers (24, 25) with a further component (2A, 2B) of the fluid (2) in order to produce the fluid (2) in the cartridge (3) by joining or mixing the components (2A, 2B),
characterized in that the cartridge (3) is only opened to remove a dose of the fluid (2) after the components (2A, 2B) have been mixed, and/or in that by mixing the components (2A, 2B), a liposomal medicament is produced in the cartridge (3).
32. Method according to aspect 31, characterized in that the mixing of the components (2A, 2B) takes place outside the nebulizer (1) or independently of the nebulizer (1), and/or in that the cartridge (3) is inserted into the nebulizer (1) and/or fluidically connected to the nebulizer (1) only after the mixing of the components (2A, 2B) and/or after the opening of the cartridge (3), and/or
in that the cartridge (3) is opened in the nebulizer (1), and/or
in that the chambers (24, 25) are fluidically connected to one another after or by inserting the cartridge (3) into the nebulizer (1), in particular by closing a housing (19) of the nebulizer (1).
33. Method according to either aspect 31 or aspect 32, characterized in that
one of the components (2A, 2B) is automatically transferred from one chamber to the other chamber (24, 25) by actuating an actuating mechanism (31), in particular by a force generated by negative pressure in one of the chambers (24, 25), and/or
in that the cartridge (3) is, after the chambers (24, 25) have been connected or after a fluid connection (30) between the chambers (24, 25) has been released, aligned such that a component (2A, 2B) is transferred from one chamber to the other chamber (24, 25)—in particular exclusively—by gravity (G), and/or
in that an actuating mechanism (31) for connecting the chambers (24, 25) is removed from the cartridge (3) after actuating the actuating mechanism (31), in particular to insert the cartridge (3) into the nebulizer (1).
34. System having a dispensing device, in particular a nebulizer (1), for dispensing a fluid (2) and a cartridge (3), wherein the fluid (2) is a medicament produced from at least two components (2A, 2B), wherein the dispensing device has a housing (19) for accommodating the cartridge (3) and a pump (9), wherein the pump (9) is designed to remove a dose of the fluid (2) from the cartridge (3) and to apply pressure to the corresponding dose for nebulizing the fluid (2), characterized in that the cartridge (3) is designed according to any of aspects 35 to 45.

35. Cartridge (3) for a dispensing device, in particular a nebulizer (1), for dispensing a fluid (2), wherein the fluid (2) is a medicament produced from at least two components (2A, 2B), wherein the cartridge (3) comprises a container (4) and a closure (6) for the fluidic and/or sealing connection of the container (4) to the dispensing device, wherein the cartridge (3) comprises at least two fluidically separated chambers (24, 25), with the chambers (24, 25) each containing at least one of the components (2A, 2B) of the fluid (2), characterized in that the cartridge (3) comprises an in particular removable actuating mechanism (31), wherein the chambers (24, 25) can be fluidically connected to one another by actuating the actuating mechanism (31) in order to produce the fluid (2) by bringing the components (2A, 2B) together.

36. Cartridge according to aspect 35, characterized in that the chambers (24, 25) in the unopened state of the cartridge (3) or the container (4) or in the stage when it is sealed from the outside or from the environment, in particular in a gastight and/or liquid-tight manner, can be fluidically connected to one another by actuating the actuating mechanism (31).

37. Cartridge according to either aspect 35 or aspect 36, characterized in that at least one of the chambers (24, 25), preferably all of the chambers (24, 25), can be reduced in size by actuating the actuating mechanism (31), and/or in that the component (2A, 2B) is at least partially transferable from one of the chambers (24, 25) to another of the chambers (24, 25).

38. Cartridge according to any of aspects 35 to 37, characterized in that the actuating mechanism (31) axially closes the cartridge (3), in particular the container (4) and/or the closure (6), and/or comprises or forms an axial end, in particular a base and/or a lid, of the cartridge (3), and/or is integrated into the container (4) or closure (6).

39. Cartridge according to any of aspects 35 to 38, characterized in that the actuating mechanism (31) comprises an actuating element (32), wherein the actuating mechanism (31) can be actuated by removing the actuating element (32) from the container (4) or closure (6), by rotating, by pushing down and/or by opening or separating the actuating element (32).

40. Cartridge according to any of aspects 35 to 39, characterized in that the actuating mechanism (31)—in particular after actuation of the actuating mechanism (31)—can be removed from the container (4) and/or closure (6), in particular twisted off or pulled off, preferably to open the cartridge (3) outward and/or to insert said cartridge into the dispensing device.

41. Cartridge according to any of aspects 35 to 40, characterized in that the actuating mechanism (31) and/or the container (4) comprises or forms at least one fluid connection (30), in particular a bypass, preferably wherein, by actuating the actuating mechanism (31), the fluid connection (30) can be released or opened and/or the chambers (24, 25) can be fluidically connected to one another via the fluid connection (30).

42. Cartridge according to any of aspects 35 to 41, characterized in that the cartridge (3), in particular the container (4) and/or the actuating mechanism (31), has at least one or two movable plungers (26, 27), preferably wherein the plunger(s) (26, 27) can be displaced by actuating the actuating mechanism (31) in the cartridge (3) or in the container (4) or in the actuating mechanism (31) and/or (each) form a wall of the chambers (24, 25).

43. Cartridge according to aspect 42, characterized in that the plunger(s) (26, 27) in the cartridge (3) or in the container (4) can be released by actuating the actuating mechanism (31), in particular such that the plunger(s) (26, 27) displace(s) automatically in the cartridge (3) or in the container (4), preferably by a force acting in the direction of one of the chambers (24, 25), particularly preferably by a tensile force, generated in particular by negative pressure in one of the chambers (24, 25).

44. Cartridge according to aspect 42, characterized in that the actuating mechanism (31), in particular the actuating element (32), is mechanically coupled to the plunger(s) (26, 27)—in particular by means of a connecting part (39)—and/or in that, by rotating the actuating mechanism (31), in particular the actuating element (32), the plunger(s) (26, 27) can be displaced in the cartridge (3), or at least one of the chambers (24, 25), preferably all of the chambers (24, 25), can be reduced in size.

45. Cartridge according to any of aspects 35 to 44, characterized in that one component (2A, 2B) is a liquid, in particular a solvent or suspension medium, and/or another component (2A, 2B) is a medicinal agent, in particular a solid, lyophilized, encapsulated and/or powdered medicinal agent.

46. Method for preparing a fluid (2) in a cartridge (3) for dispensing by means of a dispensing device, in particular a nebulizer (1), preferably wherein the cartridge (3) is designed according to any of aspects 35 to 45, wherein the fluid (2) is a medicament produced from at least two components (2A, 2B), wherein a plurality of chambers (24, 25) of the cartridge (3) which are initially fluidically separated from one another are fluidically connected to one another, wherein a component (2A, 2B) of the fluid (2) is at least partially transferred from one of the chambers (24, 25) to another of the chambers (24, 25) with a further component (2A, 2B) of the fluid (2) in order to mix the components (2A, 2B) and/or to produce the fluid (2), characterized in that the cartridge (3) is only opened to remove a dose of the fluid (2) after the components (2A, 2B) have been mixed.

47. Method according to aspect 46, characterized in that the mixing of the components (2A, 2B) takes place outside the dispensing device or independently of the dispensing device and/or that the cartridge (3) is inserted into the dispensing device and/or fluidically connected to the dispensing device only after the mixing of the components (2A, 2B) and/or the opening of the cartridge (3), and/or in that the cartridge (3) is opened in the dispensing device, and/or in that the chambers (24, 25) are fluidically connected to one another after or by inserting the cartridge (3) into the dispensing device, in particular by closing a housing (19) of the dispensing device.

48. Method according to either aspect 46 or aspect 47, characterized in that
one of the components (2A, 2B) is automatically transferred from one chamber to the other chamber (24, 25) by actuating an actuating mechanism (31), in particular by a force generated by negative pressure in one of the chambers (24, 25), and/or
in that the cartridge (3) is, after the chambers (24, 25) have been connected or after a fluid connection (30) between the chambers (24, 25) has been released, aligned such that a component (2A, 2B) is transferred from one chamber to the other chamber (24, 25)—in particular exclusively—by gravity (G), and/or
in that an actuating mechanism (31) for connecting the chambers (24, 25) is removed from the cartridge (3) after actuating the actuating mechanism (31), in particular in order to insert the cartridge (3) into the dispensing device.

Individual aspects, features and method variants or method steps of the present invention can be realized independently of one another but also in any combination or sequence.

LIST OF REFERENCE SIGNS

1 Nebulizer
2 Fluid
2A First component
2B Second component
3 Cartridge
4 Container
5 Bag
6 Closure
7 Seal
8 Connection
9 Pump
10 Drive spring
11 Holder
12 Locking element
13 Conveying element
14 One-way valve
15 Pressure chamber
16 Nozzle
17 Mouthpiece
18 Ventilation opening
19 Housing
20 Upper housing part
21 Lower housing part
22 Inner housing part
23 Ventilation means
24 First chamber
25 Second chamber
26 First plunger
27 Second plunger
28 First plunger seal
29 Second plunger seal
30 Fluid connection
31 Actuating mechanism
32 Actuating element
33 Air pump
34 Pump plunger
35 Pump cylinder
36 Pump chamber
37 Pump valve
38 Pump ventilation
39 Connecting part
39A First connecting element
39B Second connecting element
40 Ventilation
41 Base body
42 Connecting piece
43 Closure element
44 Cover
45 Opening
46 Ventilation valve
47 Conveying tube
48 Adapter
A Aerosol
G Gravity
L Longitudinal axis

The invention claimed is:

1. A cartridge (3) configured in a manner enabling complete insertion into at least one of a dispensing device and a nebulizer (1), for dispensing a fluid (2) which is a medicament produced from at least two components (2A, 2B), such that after the insertion, at least one of the dispensing device and the nebulizer encloses the cartridge on all sides of the cartridge, the cartridge (3) comprising:
a container (4) and a closure (6) for a fluidic and/or sealing connection of the container (4) to the at least one of the dispensing device and the nebulizer,
wherein the cartridge (3) comprises at least two fluidically separated chambers (24, 25), each containing at least one of the at least two components (2A, 2B) of the fluid (2),
wherein the cartridge (3) comprises an actuating mechanism (31), with the at least two fluidically separated chambers (24, 25) being able to be fluidically connected to one another by actuating the actuating mechanism (31) in order to produce the fluid (2) by bringing the at least two components (2A, 2B) together,
wherein the cartridge (3) comprises two movable plungers (26, 27),
wherein the container (4) comprises or forms at least one fluid connection (30) operating to fluidically connect the at least two fluidically separated chambers (24, 25) to one another by permitting a transfer of the first component (2A) from the first chamber (24) into the second chamber (25),
wherein the actuating mechanism (31) comprises an actuating element (32), and the actuating mechanism (31) is actuated by: (i) removing the actuating element (32) from the container (4) or closure (6); and (ii) opening or separating the actuating element (32),
wherein the actuating mechanism (31) operates to secure the plungers (26, 27) against displacement in the cartridge (3) in a non-actuated state of the actuating mechanism (31),
wherein the plungers (26, 27) in the cartridge (3) or in the container (4) are releasable for displacement by actuating the actuating mechanism (31),
wherein the fluid connection (30) operates to open by displacing the first plunger (26) and the second plunger (27) in such a way that the at least two fluidically separated chambers (24, 25) are fluidically connected to one another via the at least one fluid connection (30),
wherein the plungers (26, 27) in the cartridge (3) or in the container (4) are releasable by the actuating of the actuating mechanism (31) such that the plungers (26, 27) are displaced automatically in the cartridge (3) or in the container (4),
wherein the actuating mechanism (31) is designed such that it must be manually actuated in order to fluidically connect the at least two chambers (24, 25) to one another, and to mix the at least two components (2A, 2B) together, wherein the cartridge (3) is designed such that the manual actuation of the actuating mechanism (31) to mix the at least two components (2A, 2B) together must be achieved before the cartridge (3) is inserted into the at least one of the dispensing device and the nebulizer (1), and wherein the cartridge (3) is designed such that it is opened in the at least one of the dispensing device and the nebulizer only after removal of the actuating element (32) for a withdrawal of a dose formed of the mixed the at least two components of the fluid (2).

2. The cartridge according to claim 1, wherein the plungers (26, 27) are displaced in the cartridge (3) or in the container (4) by at least one of a force and a tensile force, acting in an axial direction of one of the at least two fluidically separated chambers (24, 25).

3. The cartridge according to claim 2, wherein the force is generated by a negative pressure in one of the at least two fluidically separated chambers (24, 25).

4. The cartridge according to claim 1, wherein the actuating mechanism (31) is actuated by rotating the actuating element (32).

5. The cartridge according to claim 1, wherein the actuating mechanism (31) is actuated by pressing down the actuating element (32).

6. The cartridge according to claim 1, wherein at least one of: (i) one component of the at least two components (2A, 2B) is at least one of a liquid and a solvent or suspension medium, and (ii) the other of the at least two components (2A, 2B) is at least one of a medicinal agent and a solid, lyophilized, encapsulated and/or powdered medicinal agent.

7. The cartridge according to claim 1, wherein at least one of the cartridge (3) and the container (4) and/or one of the plungers (26, 27), has or forms at least one of a mixing device and a stirrer, to support a mixing of the at least two components (2A, 2B).

8. A cartridge (3) configured in a manner enabling complete insertion into at least one of a dispensing device and a nebulizer (1), for dispensing a fluid (2) which is a medicament produced from at least two components (2A, 2B), such that after the insertion, at least one of the dispensing device and the nebulizer encloses the cartridge on all sides of the cartridge, the cartridge (3) comprising:

a container (4) and a closure (6) for fluidic and/or sealing connection of the container (4) to the at least one of the dispensing device and the nebulizer, wherein the cartridge (3) comprises at least two fluidically separated chambers (24, 25), each containing at least one of the at least two components (2A, 2B) of the fluid (2), wherein the cartridge (3) comprises an actuating mechanism (31), with the at least two fluidically separated chambers (24, 25) being able to be fluidically connected to one another by actuating the actuating mechanism (31) in order to produce the fluid (2) by bringing the at least two components (2A, 2B) together, wherein the cartridge (3) comprises at least one or two movable plungers (26, 27), wherein the container (4) comprises or forms at least one fluid connection (30), wherein the fluid connection (30) operates to at least one of (i) fluidically connect the at least two fluidically separated chambers (24, 25), and (ii) permit a transfer of one of the at least two components between the at least two fluidically separated chambers (24, 25), the fluid connection (30) is opened by actuating the actuating mechanism (31), and wherein, by rotating the actuating mechanism (31), or rotating an actuating element (32) of the actuating mechanism (31), the plungers (26, 27) in the cartridge (3) are displaced and at least one of the at least two fluidically separated chambers (24, 25) is reduced in size, wherein the actuating mechanism (31) is designed such that it must be manually actuated in order to fluidically connect the at least two chambers (24, 25) to one another, and to mix the at least two components (2A, 2B) together, wherein the cartridge (3) is designed such that the manual actuation of the actuating mechanism (31) to mix the at least two components (2A, 2B) together is achievable in an unopened state of the cartridge before insertion of the cartridge (3) into the at least one of the dispensing device and the nebulizer (1), and wherein the cartridge (3) is designed such that it is only opened in the at least one of the dispensing device and the nebulizer for a withdrawal of a dose of the mixed at least two components of the fluid (2).

9. The cartridge according to claim 8, wherein the actuating mechanism (31) or the actuating element (32) is mechanically coupled to the plungers (26, 27) by means of a connecting part (39).

10. The cartridge according to claim 8, wherein the actuating mechanism (31) axially closes the container (4) and/or has or forms an axial end or base, of the cartridge (3) and/or is integrated into the container (4).

11. The cartridge according to claim 8, wherein the actuating mechanism (31), after actuation of the actuating mechanism (31), is removable from the container (4) to insert the cartridge (3) into the at least one of the dispensing device and the nebulizer.

12. The cartridge according to claim 8, wherein the fluid connection (30) is a bypass.

13. A cartridge (3) configured in a manner enabling complete insertion into at least one of a dispensing device and a nebulizer (1), for dispensing a fluid (2) which is a medicament produced from at least two components (2A, 2B), such that after the insertion, at least one of the dispensing device and the nebulizer encloses the cartridge on all sides of the cartridge, the cartridge (3) comprising:

a container (4) and a closure (6) for fluidic and/or sealing connection of the container (4) to the at least one of the dispensing device and the nebulizer, wherein the cartridge (3) comprises at least two fluidically separated chambers (24, 25), each containing at least one of the at least two components (2A, 2B) of the fluid (2), wherein the cartridge (3) comprises an actuating mechanism (31), with the at least two fluidically separated chambers (24, 25) being able to be fluidically connected to one another by actuating the actuating mechanism (31) in order to produce the fluid (2) by bringing the at least two components (2A, 2B) together, wherein the cartridge (3) has at least one movable plunger (26), wherein the container (4) comprises or forms at least one fluid connection (30), wherein the fluid connection (30) operates to at least one of (i) fluidically connect the at least two fluidically separated chambers (24, 25), and (ii) permit a transfer of one of the at least two components between the at least two fluidically separated chambers (24, 25), wherein, by actuating the actuating mechanism (31), at least one of: (i) the fluid connection (30) is opened, and (ii) the at least two chambers (24, 25) are fluidically connected to one another via the fluid connection (30), wherein the actuating mechanism (31) is integrated into the closure (6), and wherein the actuating mechanism (31) is actuated by pressing down the at least one movable plunger (26), wherein the actuating mechanism (31) is designed such that it must be manually actuated in order to fluidically connect the at least two chambers (24, 25) to one another, and to mix the at least two components (2A, 2B) together, wherein the cartridge (3) is designed such that the manual actuation of the actuating mechanism (31) to mix the at least two components (2A, 2B) together must be achieved before the cartridge (3) is inserted into the at least one of the at least one of the dispensing device and the nebulizer and the nebulizer (1), and wherein the cartridge (3) is designed such that it is opened in the at least one of the dispensing device and the nebulizer only after pressing down the at least one movable plunger of the cartridge the actuating mechanism (31) for a withdrawal of a dose formed of the mixed at least two components of the fluid (2).

14. The cartridge according to claim 13, wherein at least one of: (i) one of the at least two fluidically separated chambers (24, 25) is integrated into the actuating mechanism (31); and (ii) the actuating mechanism (31) contains one of the at least two fluidically separated chambers (24, 25) or one of the at least two components (2A, 2B).

15. The cartridge according to claim 14, wherein at least one of: (i) one of the at least two fluidically separated chambers (25, 24) is formed by the container (4); and (ii) the container (4) contains one of the at least two components (2B, 2A).

16. The cartridge according to claim 13, wherein the actuating mechanism (31), after actuation of the actuating mechanism (31), is removable from the closure (6), to open the cartridge (3) outward and/or to insert said cartridge into the at least one of the dispensing device and the nebulizer.

17. The cartridge according to claim 13, wherein the actuating mechanism (31) comprises or forms at least one fluid connection (30), and wherein by actuating the actuating mechanism (31), the fluid connection (30) is released or opened and/or the at least two fluidically separated chambers (24, 25) is fluidically connected to one another via the fluid connection (30).

18. The cartridge according to claim 13, wherein the at least one movable plunger (26) forms a wall of the at least two fluidically separated chambers (24, 25).

19. The cartridge according to claim 13, wherein the actuating mechanism (31) is removable.

20. The cartridge according to claim 13, wherein the at least two fluidically separated chambers (24, 25) in the unopened state of the cartridge (3) or the container (4) or in the stage when it is sealed from the outside or from the environment in a gastight and/or liquid-tight manner, are fluidically connected to one another by actuating the actuating mechanism (31).

21. The cartridge according to claim 13, wherein at least one of the at least two fluidically separated chambers (24, 25) is reducible in size by actuating the actuating mechanism (31).

22. The cartridge according to claim 13, wherein all of the at least two fluidically separated chambers (24, 25) are reducible in size by actuating the actuating mechanism (31).

23. The cartridge according to claim 13, wherein the at least two components (2A, 2B) are at least partially transferrable from one of the at least two fluidically separated chambers (24, 25) to another of the at least two fluidically separated chambers (24, 25).

24. The cartridge according to claim 13, wherein a liposomal medicament is producible as the fluid (2) by bringing the at least two components (2A, 2B) together.

25. The cartridge according to claim 13, wherein a first of the at least two fluidically separated chambers (24) contains at least one of a solution and an ethanolic lipid solution, as a first of the at least two components (2A) of the medicament, and a second of the at least two fluidically separated chambers (25) contains an aqueous buffer as a second of at least two components (2B) in order to produce a liposomal medicament by combining the at least two components (2A, 2B).

26. A system having a cartridge (3) configured in a manner enabling complete insertion into at least one of a dispensing device and a nebulizer (1), for dispensing a fluid (2) which is a medicament produced from at least two components (2A, 2B), such that after the insertion, at least one of the dispensing device and the nebulizer encloses the cartridge on all sides of the cartridge, wherein the at least one of the dispensing device and the nebulizer has a housing (19) for accommodating the cartridge (3) and a pump (9), wherein the pump (9) is designed to remove a dose of the fluid (2) from the cartridge (3) and to apply pressure to the corresponding dose for dispensing the fluid (2), and wherein the cartridge (3) comprises:

a container (4) and a closure (6) for fluidic and/or sealing connection of the container (4) to the at least one of the dispensing device and the nebulizer, wherein the cartridge (3) comprises at least two fluidically separated chambers (24, 25), each containing at least one of the at least two components (2A, 2B) of the fluid (2), wherein the cartridge (3) comprises an actuating mechanism (31), with the at least two fluidically separated chambers (24, 25) being able to be fluidically connected to one another by actuating the actuating mechanism (31) in order to produce the fluid (2) by bringing the at least two components (2A, 2B) together, wherein the cartridge (3) comprises two movable plungers (26, 27), wherein the container (4) comprises or forms at least one fluid connection (30) operating to fluidically connect the at least two fluidically separated chambers (24, 25) to one another by permitting a transfer of the first component (2A) from the first chamber (24) into the second chamber (25), wherein the actuating mechanism (31) comprises an actuating element (32), and the actuating mechanism (31) is actuated by: (i) removing the actuating element (32) from the container (4) or closure (6); and (ii) opening or separating the actuating element (32), wherein the actuating mechanism (31) operates to secure the plungers (26, 27) against displacement in the cartridge (3) in a non-actuated state of the actuating mechanism (31), wherein the plungers (26, 27) in the cartridge (3) or in the container (4) are releasable for displacement by actuating the actuating mechanism (31), wherein the fluid connection (30) operates to open by displacing the first plunger (26) and the second plunger (27) in such a way that the at least two fluidically separated chambers (24, 25) are fluidically connected to one another via the at least one fluid connection (30), and wherein the plungers (26, 27) in the cartridge (3) or in the container (4) are releasable by actuating the actuating mechanism (31) such that the plungers (26, 27) are displaced automatically in the cartridge (3) or in the container (4), wherein the actuating mechanism (31) is designed such that it must be manually actuated in order to fluidically connect the at least two chambers (24, 25) to one another, and to mix the at least two components (2A, 2B) together, wherein the cartridge (3) is designed such that the manual actuation of the actuating mechanism (31) to mix the at least two components (2A, 2B) together must be achieved before the cartridge (3) is inserted into the at least one of the at least one of the dispensing device and the nebulizer and the nebulizer (1), and wherein the cartridge (3) is designed such that it is opened in the at least one of the dispensing device and the nebulizer for a withdrawal of a dose formed of the mixed components of the fluid (2) only after removal of the of the actuating element (32).

27. A method for preparing a fluid (2) which is a medicament produced from at least two components (2A, 2B) in a cartridge (3) which is completely inserted into at least one of a dispensing device and a nebulizer (1), such that after the insertion, at least one of the dispensing device and the nebulizer encloses the cartridge on all sides of the cartridge, wherein the cartridge (3) comprises:
a seal (7),
a container (4) and a closure (6) for fluidic and/or sealing connection of the container (4) to the at least one of the dispensing device and the nebulizer,
wherein the cartridge (3) comprises at least two fluidically separated chambers (24, 25), each containing at least one of the at least two components (2A, 2B) of the fluid (2),
wherein the cartridge (3) comprises an actuating mechanism (31), with the at least two fluidically separated chambers (24, 25) being able to be fluidically connected to one another by actuating the actuating mechanism (31) in order to produce the fluid (2) by bringing the at least two components (2A, 2B) together,
wherein the cartridge (3) comprises two movable plungers (26, 27),
wherein the container (4) comprises or forms at least one fluid connection (30) operating to fluidically connect the at least two fluidically separated chambers (24, 25) to one another by permitting a transfer of the first component (2A) from the first chamber (24) into the second chamber (25),
wherein the actuating mechanism (31) comprises an actuating element (32), and the actuating mechanism (31) is actuated by: (i) removing the actuating element (32) from the container (4) or closure (6); and (ii) opening or separating the actuating element (32),
wherein the actuating mechanism (31) operates to secure the plungers (26, 27) against displacement in the cartridge (3) in a non-actuated state of the actuating mechanism (31),
wherein the plungers (26, 27) in the cartridge (3) or in the container (4) are releasable for displacement by actuating the actuating mechanism (31),
wherein the fluid connection (30) operates to open by displacing the first plunger (26) and the second plunger (27) in such a way that the at least two fluidically separated chambers (24, 25) are fluidically connected to one another via the at least one fluid connection (30), and
wherein the plungers (26, 27) in the cartridge (3) or in the container (4) are releasable by actuating the actuating mechanism (31) such that the plungers (26, 27) are displaced automatically in the cartridge (3) or in the container (4),
wherein the at least two fluidically separated chambers (24, 25) of the cartridge (3) which are initially fluidically separated from one another are fluidically connected to one another,
wherein at least one of the at least two components (2A, 2B) of the fluid (2) is at least partially transferred from one of the at least two fluidically separated chambers (24, 25) to another of the at least two fluidically separated chambers (24, 25) with a further one of the at least one of the at least two components (2A, 2B) of the fluid (2) in order to mix the at least two components (2A, 2B) and/or to produce the fluid (2),
wherein the actuating mechanism (31) is manually actuated in order to fluidically connect the at least two chambers (24, 25) to one another, and to mix the at least two components (2A, 2B) together,
wherein the cartridge (3) is only inserted into the at least one of the dispensing device and the nebulizer after the at least two components (2A, 2B) have been mixed, and is only thereafter opened in the at least one of the dispensing device and the nebulizer for a withdrawal of a dose of the fluid (2) only after the actuating element has been removed, and
wherein opening of the cartridge (3) is achieved by piercing, the seal (7).

28. The method according to claim 27, wherein the at least two components (2A, 2B) are mixed outside the at least one of the dispensing device and the nebulizer or independently of the at least one of the dispensing device and the nebulizer.

29. The method according to claim 27, wherein the cartridge (3) is fluidically connected to the at least one of the dispensing device and the nebulizer only after the at least two components (2A, 2B) have been mixed.

30. The method according to claim 27, wherein the cartridge (3) is fluidically connected to the at least one of the dispensing device and the nebulizer only after the cartridge (3) has been opened.

31. The method according to claim 27, wherein one of the at least two components (2A, 2B) is automatically transferred from one of the at least two fluidically separated chambers to another of the at least two fluidically separated chambers (24, 25) by actuating an actuating mechanism (31).

32. The method according to claim 31, wherein one of the at least two components (2A, 2B) is transferred from one of the at least two fluidically separated chambers to another of the at least two fluidically separated chambers (24, 25) by a force generated by negative pressure in one of the at least two fluidically separated chambers (24, 25).

33. The method according to claim 27, wherein the cartridge (3) is, after the at least two fluidically separated chambers (24, 25) have been connected or after a fluid connection (30) between the at least two fluidically separated chambers (24, 25) has been released, aligned such that one of the at least two components (2A, 2B) is transferred from one of the at least two fluidically separated chambers to another of the at least two fluidically separated chambers (24, 25) by gravity (G).

34. The method according to claim 27, wherein the actuating mechanism (31) for connecting the at least two fluidically separated chambers (24, 25) is removed from the cartridge (3) after the actuating mechanism (31) has been actuated in order to insert the cartridge (3) into the at least one of the dispensing device and the nebulizer.

35. The method according to claim 27, wherein, by mixing the at least two components (2A, 2B), a liposomal medicament is produced in the cartridge (3).

* * * * *